United States Patent
Freel et al.

(10) Patent No.: US 12,234,410 B2
(45) Date of Patent: Feb. 25, 2025

(54) SYSTEMS AND METHODS FOR FORMALDEHYDE CONTROL

(71) Applicant: KERRY GROUP SERVICES INTERNATIONAL LIMITED, Tralee (IE)

(72) Inventors: Barry A. Freel, Ottawa (CA); Satya T. Jujjuri, Wilmington, DE (US); Douglas A. Clarke, Ottawa (CA)

(73) Assignee: Kerry Group Services International Limited, Co. Kerry (IE)

(*) Notice: Subject to any disclaimer, the term of this patent is extended or adjusted under 35 U.S.C. 154(b) by 0 days.

(21) Appl. No.: 17/130,699

(22) Filed: Dec. 22, 2020

(65) Prior Publication Data

US 2021/0189247 A1    Jun. 24, 2021

Related U.S. Application Data

(60) Provisional application No. 62/952,876, filed on Dec. 23, 2019.

(51) Int. Cl.
| | |
|---|---|
| *C10B 57/04* | (2006.01) |
| *C07C 45/51* | (2006.01) |
| *C07C 47/04* | (2006.01) |
| *C07C 47/19* | (2006.01) |
| *C10B 49/22* | (2006.01) |
| *C10B 53/02* | (2006.01) |
| *C10K 1/00* | (2006.01) |

(52) U.S. Cl.
CPC ............. *C10B 49/22* (2013.01); *C07C 45/51* (2013.01); *C10B 53/02* (2013.01); *C10B 57/04* (2013.01); *C10K 1/001* (2013.01); *C10K 1/002* (2013.01); *C07C 47/04* (2013.01); *C07C 47/19* (2013.01)

(58) Field of Classification Search
CPC ......... C10B 53/02; C10B 49/10; C10B 47/24; C07C 45/51–55
See application file for complete search history.

(56) References Cited

U.S. PATENT DOCUMENTS

| | | | | |
|---|---|---|---|---|
| 5,252,188 | A * | 10/1993 | Stradal | C07C 45/51 203/91 |
| 5,397,582 | A * | 3/1995 | Underwood | A23B 4/048 426/271 |
| 5,728,271 | A * | 3/1998 | Piskorz | C10G 1/10 201/31 |
| 5,792,340 | A * | 8/1998 | Freel | C10B 49/20 208/126 |
| 5,952,029 | A * | 9/1999 | Freel | A23L 27/201 426/314 |
| 5,961,786 | A * | 10/1999 | Freel | C10B 49/22 208/126 |

(Continued)

OTHER PUBLICATIONS

S. Czernik and A. V. Bridgwater, Overview of Applications of Biomass Fast Pyrolysis Oil, Energy & Fuels, 2004 18 (2), 590-598, DOI: 10.1021/ef034067u.*

(Continued)

*Primary Examiner* — Jonathan Luke Pilcher
(74) *Attorney, Agent, or Firm* — Sughrue Mion, PLLC

(57) ABSTRACT

Methods are provided to use water-free quench liquids to obtain pyrolytic liquid products with reduced formaldehyde content. Products include liquids with improved hydroxyacetaldehyde content.

19 Claims, 4 Drawing Sheets

(56) References Cited

U.S. PATENT DOCUMENTS

| | | | | |
|---|---|---|---|---|
| 6,316,040 B1* | 11/2001 | Freel | A23L 27/201 | 426/314 |
| 6,326,461 B1* | 12/2001 | Giroux | C09J 161/24 | 536/127 |
| 6,485,841 B1* | 11/2002 | Freel | C10L 1/02 | 106/18.32 |
| 6,555,649 B2 | 4/2003 | Giroux | C08L 61/24 | 530/200 |
| 6,844,420 B1* | 1/2005 | Freel | C08G 16/0293 | 530/200 |
| 7,094,932 B2* | 8/2006 | Majerski | C07C 45/673 | 568/465 |
| 7,199,080 B2* | 4/2007 | Freel | C01B 32/336 | 502/423 |
| 7,270,743 B2* | 9/2007 | Freel | C10G 31/06 | 208/410 |
| 7,572,362 B2* | 8/2009 | Freel | C10G 51/023 | 208/126 |
| 7,572,365 B2* | 8/2009 | Freel | C10G 51/023 | 208/126 |
| 7,905,990 B2* | 3/2011 | Freel | C10B 49/22 | 585/242 |
| 8,062,503 B2* | 11/2011 | Freel | C10G 9/30 | 208/126 |
| 8,097,090 B2* | 1/2012 | Freel | B08B 9/00 | 110/344 |
| 8,105,482 B1* | 1/2012 | Freel | C10G 9/32 | 208/126 |
| 8,499,702 B2* | 8/2013 | Palmas | C10B 53/02 | 110/244 |
| 8,519,205 B2* | 8/2013 | Frey | C10L 1/026 | 585/242 |
| 8,726,443 B2* | 5/2014 | Freel | B08B 9/045 | 15/104.05 |
| 8,936,654 B2* | 1/2015 | Platon | C10C 5/00 | 585/242 |
| 8,940,060 B2* | 1/2015 | Baird | C10K 1/08 | 585/242 |
| 8,961,743 B2* | 2/2015 | Freel | C10B 57/00 | 202/121 |
| 9,005,428 B2* | 4/2015 | Freel | C10G 9/30 | 208/126 |
| 9,102,888 B2* | 8/2015 | Freel | C10G 3/42 | |
| 9,102,889 B2* | 8/2015 | Freel | B01J 8/0055 | |
| 9,102,890 B2* | 8/2015 | Freel | C10L 1/04 | |
| 9,109,177 B2* | 8/2015 | Freel | C10L 1/1802 | |
| 9,120,988 B2* | 9/2015 | Freel | C10L 1/06 | |
| 9,120,989 B2* | 9/2015 | Freel | C10G 11/00 | |
| 9,120,990 B2* | 9/2015 | Freel | C10L 1/1802 | |
| 9,127,208 B2* | 9/2015 | Boulard | C10C 5/00 | |
| 9,127,223 B2* | 9/2015 | Freel | C10L 1/06 | |
| 9,127,224 B2* | 9/2015 | Freel | C10L 1/1802 | |
| 9,410,091 B2* | 8/2016 | Freel | C10G 1/00 | |
| 9,422,478 B2* | 8/2016 | Palmas | C10C 5/00 | |
| 9,422,485 B2* | 8/2016 | Freel | C10L 1/1616 | |
| 9,631,145 B2* | 4/2017 | Freel | C10K 1/04 | |
| 9,670,413 B2* | 6/2017 | Baird | C10B 53/02 | |
| 9,719,021 B2* | 8/2017 | Freel | C10G 9/32 | |
| 9,796,649 B2* | 10/2017 | Taarning | C07C 209/24 | |
| 9,809,564 B2* | 11/2017 | Boulard | C10C 5/00 | |
| 9,969,942 B2* | 5/2018 | Freel | B01J 4/002 | |
| 10,337,726 B2* | 7/2019 | Freel | F23D 11/445 | |
| 10,400,176 B2* | 9/2019 | Freel | C07C 7/09 | |
| 10,544,368 B2* | 1/2020 | Freel | C10B 57/00 | |
| 10,570,340 B2* | 2/2020 | Freel | C10L 1/1817 | |
| 10,589,187 B2* | 3/2020 | Bélanger | C10K 1/04 | |
| 10,633,606 B2* | 4/2020 | Freel | C10G 11/18 | |
| 10,640,719 B2* | 5/2020 | Freel | C10L 1/04 | |
| 10,767,114 B2* | 9/2020 | Bélanger | C10K 1/18 | |
| 10,948,179 B2* | 3/2021 | Freel | F23D 11/24 | |
| 10,975,315 B2* | 4/2021 | Freel | C10G 1/002 | |
| 10,982,152 B2* | 4/2021 | Freel | C07C 7/09 | |
| 2002/0132972 A1* | 9/2002 | Giroux | C08H 8/00 | 530/200 |
| 2004/0022912 A1* | 2/2004 | Majerski | C07C 47/19 | 426/534 |
| 2004/0097369 A1* | 5/2004 | Freel | C01B 32/336 | 502/437 |
| 2007/0125369 A1* | 6/2007 | Olson | C13K 1/02 | 127/37 |
| 2009/0139851 A1* | 6/2009 | Freel | F28C 3/08 | 201/23 |
| 2009/0266380 A1* | 10/2009 | Freel | B08B 9/045 | 134/8 |
| 2010/0236915 A1* | 9/2010 | Freel | F23J 3/02 | 202/241 |
| 2011/0123407 A1* | 5/2011 | Freel | F28C 3/08 | 422/187 |
| 2012/0012039 A1* | 1/2012 | Palmas | C10B 53/02 | 110/259 |
| 2012/0167452 A1* | 7/2012 | Platon | B01D 53/1487 | 252/364 |
| 2013/0145683 A1* | 6/2013 | Freel | C10L 1/04 | 44/307 |
| 2013/0152455 A1* | 6/2013 | Baird | C10B 49/16 | 422/187 |
| 2013/0327629 A1* | 12/2013 | Palmas | C10B 53/02 | 201/16 |
| 2013/0333278 A1* | 12/2013 | Frey | C10B 49/22 | 44/307 |
| 2014/0001026 A1* | 1/2014 | Baird | C10B 49/10 | 202/96 |
| 2014/0053456 A1* | 2/2014 | Hopkins | C10G 7/02 | 208/92 |
| 2014/0352204 A1* | 12/2014 | Belanger | C10C 5/00 | 422/187 |
| 2015/0000186 A1* | 1/2015 | Freel | C10L 1/06 | 44/307 |
| 2015/0004062 A1* | 1/2015 | Freel | C10L 1/1616 | 422/119 |
| 2015/0004067 A1* | 1/2015 | Freel | C10G 65/043 | 422/139 |
| 2015/0005547 A1* | 1/2015 | Freel | C10G 3/00 | 585/14 |
| 2015/0005548 A1* | 1/2015 | Freel | B01J 8/26 | 585/14 |
| 2015/0005549 A1* | 1/2015 | Freel | B01J 4/008 | 585/242 |
| 2015/0059235 A1* | 3/2015 | Freel | C10G 45/02 | 44/307 |
| 2015/0065759 A1* | 3/2015 | Freel | B01J 8/0055 | 585/13 |
| 2015/0065760 A1* | 3/2015 | Freel | B01J 4/002 | 422/310 |
| 2015/0066731 A1* | 3/2015 | Freel | B01J 4/002 | 705/37 |
| 2015/0068107 A1* | 3/2015 | Freel | G06Q 50/06 | 44/307 |
| 2015/0107150 A1* | 4/2015 | Belanger | C10L 1/026 | 202/109 |
| 2015/0191656 A1* | 7/2015 | Freel | C10B 57/00 | 165/104.13 |
| 2016/0002137 A1* | 1/2016 | Taarning | C07H 3/02 | 426/268 |
| 2016/0040080 A1* | 2/2016 | Freel | C10L 1/06 | 585/254 |
| 2016/0355739 A1* | 12/2016 | Freel | C10G 1/00 | |
| 2017/0051912 A1* | 2/2017 | Freel | F23C 1/00 | |
| 2017/0275545 A1* | 9/2017 | Freel | C10G 3/57 | |
| 2018/0030356 A1* | 2/2018 | Freel | C10B 49/22 | |
| 2018/0334618 A1* | 11/2018 | Freel | C10B 53/02 | |
| 2019/0078026 A1* | 3/2019 | Freel | C10L 1/1802 | |
| 2019/0144773 A1* | 5/2019 | Ribeiro De Lima | C10L 5/442 | 44/590 |
| 2019/0162404 A1* | 5/2019 | Freel | F23M 20/00 | |
| 2020/0010764 A1* | 1/2020 | Freel | C10B 53/02 | |
| 2020/0190406 A1* | 6/2020 | Freel | C10B 49/22 | |

(56) References Cited

U.S. PATENT DOCUMENTS

| | | | |
|---|---|---|---|
| 2020/0255746 A1* | 8/2020 | Freel | C10L 1/06 |
| 2021/0189247 A1* | 6/2021 | Freel | C10K 1/04 |
| 2021/0348065 A1* | 11/2021 | Freel | C10G 11/00 |

OTHER PUBLICATIONS

Shaw DG; Hydrocarbons with Water and Seawater. Part II: Hydrocarbons C8 to C36. International Union of Pure and Applied Chemistry. Solubility Data Series. vol 38 p. 326 (1989).*

Roel J. M. Westerhof, Norbert J. M. Kuipers, Sascha R. A. Kersten, and Wim P. M. van Swaaij, "Controlling the Water Content of Biomass Fast Pyrolysis Oil", Industrial & Engineering Chemistry Research, 2007 46 (26), 9238-9247, DOI: 10.1021/ie070684k.*

"Diesel vs Petrol." Diffen.com. Diffen LLC, n.d. Web. Mar. 17, 2024. < https://www.diffen.com/difference/Diesel_vs_Petrol >.*

* cited by examiner

SYSTEMS AND METHODS FOR FORMALDEHYDE CONTROL

CROSS-REFERENCE TO RELATED APPLICATION

This application claims the benefit of U.S. Provisional Application No. 62/952,876, filed Dec. 23, 2019, the contents which is incorporated herein by reference in its entirety.

FIELD OF THE INVENTION

The present invention relates to formaldehyde reduction in liquid products derived from thermal conversion of biomass.

BACKGROUND OF THE INVENTION

The U.S. Environmental Protection Agency (EPA) lists formaldehyde as a suspected human carcinogen, and animal studies have shown an increased incidence of nasal and lung cancers from inhaled formaldehyde. Some liquid products of conventional biomass pyrolysis contain formaldehyde at levels that may lead to excessive exposure in certain workplace environments. U.S. Patent Application No. 2004/0022912, for example, discloses products rich in acetaldehyde (a food browning agent) having formaldehyde concentrations as high as 1.9 wt. % formed by pyrolysis of 34 wt. % aqueous glucose. U.S. Patent Application No. 2016/0002137 discloses products having formaldehyde concentrations as high as 6.8 g/L formed by pyrolysis of 10 wt. % aqueous glucose. Depending on how these products were to be handled in different facilities, they could potentially introduce formaldehyde into the workplace in excess of the U.S. Occupational Safety and Health Administration (OSHA) actionable limit of 0.5 parts per million (ppm) in air under, 37 C.F.R. § 1910.1048, or even the Permissible Exposure Limit (PEL) of 0.75 ppm of air time-weighted for an 8-hour period. In Europe, the trade group Formacare and the European Chemical Employers Group have agreed to implement an EU-wide binding occupational exposure limit of 0.3 ppm for an 8-hour average and 0.6 ppm for short term exposure. Further European legislation is also anticipated. Accordingly, systems and methods for production of valuable products with reduced formaldehyde concentration are desirable.

BRIEF SUMMARY OF THE INVENTION

Certain embodiments may provide, for example, a method for producing a low-formaldehyde product having a ratio of no more than 150 ppm (for example no more than 100 ppm or no more than 0 ppm) formaldehyde per 1° BX of the low-formaldehyde product. In certain embodiments, for example, the method may comprise: pyrolyzing biomass (for example one or more of the biomasses disclosed in the INCORPORATED REFERENCES) to form gaseous pyrolysis products. In certain embodiments, for example, the method may comprise: condensing a portion of the gaseous pyrolysis products to form the low-formaldehyde product, comprising: contacting the gaseous pyrolysis products with a nonaqueous quench media (or coolant). In certain embodiments, for example, the method may comprise: separating at least a portion of the low-formaldehyde product from the nonaqueous quench media (or coolant).

A. In certain embodiments, for example, the biomass may comprise one or more sugars and/or one or more starches. In certain embodiments, for example, the one or more sugars may comprise a simple sugar. In certain embodiments, for example, the one or more sugars may comprise glucose. In certain embodiments, for example, the one or more sugars may be glucose. In certain embodiments, for example, the biomass may comprise an impure mixture of different sugars. In certain embodiments, for example, the one or more starches may comprise one or more of corn starch, potato starch, wheat starch, oat starch, tapioca starch and rice starch. In certain embodiments, for example, the biomass may comprise a cellulosic biomass. In certain embodiments, for example, the biomass may comprise a wood. In certain embodiments, for example, the biomass may comprise sawdust. In certain embodiments, for example, the biomass may be a complex biomass (for example in a potato, sugar beet, etc.).

In certain embodiments, for example, the biomass may be provided in a solution. In certain embodiments, for example, the solution may have a BRIX value of at least 10° BX, for example the solution may have a BRIX value of at least 20° BX, of at least 30° BX, of at least 40° BX, of at least 50° BX, of at least 60° BX, of at least 65° BX, of at least 70° BX, of at least 80° BX, or the solution may have a BRIX value of at least 90° BX. In certain embodiments, for example, the solution may have a BRIX value of between 40° BX and 80° BX, for example the solution may have a BRIX value of between 40° BX and 75° BX, of between 40° BX and 70° BX, of between 50° BX and 70° BX, or the solution may have a BRIX value of between 60° BX and 75° BX. In certain embodiments, for example the solution may be preheated to a temperature of between 30° C. and 90° C. prior to introducing the solution to a pyrolysis reactor, for example the solution may be preheated to a temperature of between 40° C. and 90° C., between 50° C. and 90° C., between 60° C. and 90° C., between 70° C. and 90° C., or the solution may be preheated to a temperature of between 75° C. and 85° C. prior to introducing the solution to a pyrolysis reactor.

In certain embodiments, for example, the biomass may be provided in a particulate solid. In certain embodiments, for example, the particulate solid may be provided in a fluidization gas. In certain embodiments, for example the fluidization gas may be cooled (for example to prevent the particulate solid from forming deposits such as coke near the inlet to a pyrolysis reactor or reduce such forming near the inlet to a pyrolysis reactor) to a temperature of between −40° C. and 10° C. prior to introducing the particulate solid and the carrier gas to a pyrolysis reactor, for example the carrier gas may be preheated to a temperature of between 40° C. and 90° C., between 50° C. and 90° C., between 60° C. and 90° C., between 70° C. and 90° C., or the carrier gas may be preheated to a temperature of between 75° C. and 85° C. prior to introducing the particulate solid and the carrier gas to a pyrolysis reactor.

In certain embodiments, for example, the biomass may be provided in a liquid. In certain embodiments, for example, the biomass may be provided in a syrup. In certain embodiments, for example, the biomass may be provided in a suspension (for example particles containing the biomass suspended in a liquid).

B. In certain embodiments, for example, the low-formaldehyde product may have a ratio of no more than 140 ppm formaldehyde per 1° BX of the low-formaldehyde product, for example the low-formaldehyde product may have a ratio of no more than 100 ppm formaldehyde per 1° BX of the low-formaldehyde product, a ratio of no more than 90 ppm formaldehyde per 1° BX of the low-formaldehyde product, a ratio of no more than 80 ppm formaldehyde per 1° BX of the low-formaldehyde product, a ratio of no more than 70 ppm formaldehyde per 1° BX of the low-formaldehyde product, a ratio of no more than 60 ppm formaldehyde per 1° BX of the low-formaldehyde product, a ratio of no more than 50 ppm formaldehyde per 1° BX of the low-formaldehyde product, a ratio of no more than 40 ppm formaldehyde per 1° BX of the low-formaldehyde product, a ratio of no more than 30 ppm formaldehyde per 1° BX of the low-formaldehyde product, a ratio of no more than 20 ppm formaldehyde per 1° BX of the low-formaldehyde product, a ratio of no more than 10 ppm formaldehyde per 1° BX of the low-formaldehyde product, or the low-formaldehyde product may have a ratio of no more than 5 ppm formaldehyde per 1° BX of the low-formaldehyde product. In certain embodiments, for example, the low-formaldehyde product may have a ratio of between 10 ppm formaldehyde per 1° BX of the low-formaldehyde product and 150 ppm formaldehyde per 1° BX of the low-formaldehyde product, for example the low-formaldehyde product may have a ratio of between 10 ppm formaldehyde per 1° BX of the low-formaldehyde product and 100 ppm formaldehyde per 1° BX of the low-formaldehyde product, of between 20 ppm formaldehyde per 1° BX of the low-formaldehyde product and 75 ppm formaldehyde per 1° BX of the low-formaldehyde product, of between 10 ppm formaldehyde per 1° BX of the low-formaldehyde product and 75 ppm formaldehyde per 1° BX of the low-formaldehyde product, of between 20 ppm formaldehyde per 1° BX of the low-formaldehyde product and 75 ppm formaldehyde per 1° BX of the low-formaldehyde product, of between 10 ppm formaldehyde per 1° BX of the low-formaldehyde product and 50 ppm formaldehyde per 1° BX of the low-formaldehyde product, of between 20 ppm formaldehyde per 1° BX of the low-formaldehyde product and 50 ppm formaldehyde per 1° BX of the low-formaldehyde product, of between 25 ppm formaldehyde per 1° BX of the low-formaldehyde product and 40 ppm formaldehyde per 1° BX of the low-formaldehyde product, of between 50 ppm formaldehyde per 1° BX of the low-formaldehyde product and 150 ppm formaldehyde per 1° BX of the low-formaldehyde product, of between 50 ppm formaldehyde per 1° BX of the low-formaldehyde product and 125 ppm formaldehyde per 1° BX of the low-formaldehyde product, of between 60 ppm formaldehyde per 1° BX of the low-formaldehyde product and 100 ppm formaldehyde per 1° BX of the low-formaldehyde product, of between 50 ppm formaldehyde per 1° BX of the low-formaldehyde product and 90 ppm formaldehyde per 1° BX of the low-formaldehyde product, of between 70 ppm formaldehyde per 1° BX of the low-formaldehyde product and 100 ppm formaldehyde per 1° BX of the low-formaldehyde product, or the low-formaldehyde product may have a ratio of between 75 ppm formaldehyde per 1° BX of the low-formaldehyde product and 95 ppm formaldehyde per 1° BX of the low-formaldehyde product.

In certain embodiments, for example, the low-formaldehyde product may have a ratio of formaldehyde-to-hydroxyacetaldehyde of no more than 0.1 (w/w), for example the low-formaldehyde product may have a ratio of formaldehyde-to-hydroxyacetaldehyde of no more than 0.09 (w/w), of no more than 0.08 (w/w), of no more than 0.07 (w/w), of no more than 0.06 (w/w), of no more than 0.05 (w/w), of no more than 0.04 (w/w), of no more than 0.03 (w/w), of no more than 0.02 (w/w), of no more than 0.018 (w/w), of no more than 0.017 (w/w), of no more than 0.016 (w/w), of no more than 0.015 (w/w), of no more than 0.014 (w/w), of no more than 0.013 (w/w), of no more than 0.012 (w/w), of no more than 0.011 (w/w), of no more than 0.010 (w/w), of no more than 0.009 (w/w), of no more than 0.008 (w/w), of no more than 0.007 (w/w), of no more than 0.006 (w/w), of no more than 0.005 (w/w), of no more than 0.004 (w/w), of no more than 0.003 (w/w), of no more than 0.002 (w/w), or the low-formaldehyde product may have a ratio of formaldehyde-to-hydroxyacetaldehyde of no more than 0.001 (w/w). In certain embodiments, for example, the low-formaldehyde product may have a ratio of formaldehyde-to-hydroxyacetaldehyde of between 0.001 (w/w) and 0.1 (w/w), for example a ratio of formaldehyde-to-hydroxyacetaldehyde of between 0.001 (w/w) and 0.09 (w/w), of between 0.001 (w/w) and 0.08 (w/w), of between 0.001 (w/w) and 0.07 (w/w), of between 0.001 (w/w) and 0.06 (w/w), of between 0.001 (w/w) and 0.05 (w/w), of between 0.001 (w/w) and 0.04 (w/w), of between 0.001 (w/w) and 0.03 (w/w), of between 0.005 (w/w) and 0.02 (w/w), of between 0.01 (w/w) and 0.02 (w/w), of between 0.015 (w/w) and 0.02 (w/w), of between 0.01 (w/w) and 0.015 (w/w), of between 0.015 (w/w) and 0.018 (w/w), or the low-formaldehyde product may have a ratio of formaldehyde-to-hydroxyacetaldehyde of between 0.016 (w/w) and 0.019 (w/w).

In certain embodiments, for example, the low-formaldehyde product may have a ratio of at least 0.01 wt. % hydroxyacetaldehyde per 1° BX of the low-formaldehyde product, for example, the low-formaldehyde product may have a ratio of at least 0.05 wt. % hydroxyacetaldehyde per 1° BX of the low-formaldehyde product, of at least 0.1 wt. % hydroxyacetaldehyde per 1° BX of the low-formaldehyde product, of at least 0.2 wt. % hydroxyacetaldehyde per 1° BX of the low-formaldehyde product, of at least 0.3 wt. % hydroxyacetaldehyde per 1° BX of the low-formaldehyde product, of at least 0.35 wt. % hydroxyacetaldehyde per 1° BX of the low-formaldehyde product, of at least 0.4 wt. % hydroxyacetaldehyde per 1° BX of the low-formaldehyde product, of at least 0.45 wt. % hydroxyacetaldehyde per 1° BX of the low-formaldehyde product, or the low-formaldehyde product may have a ratio of at least 0.5 wt. % hydroxyacetaldehyde per 1° BX of the low-formaldehyde product. In certain embodiments, for example, the low-formaldehyde product may have a ratio of between 0.05 wt. % hydroxyacetaldehyde per 1° BX of the low-formaldehyde product and 0.5 wt. % hydroxyacetaldehyde per 1° BX of the low-formaldehyde product, for example the low-formaldehyde product may have a ratio of between 0.1 wt. % hydroxyacetaldehyde per 1° BX of the low-formaldehyde product and 0.5 wt. % hydroxyacetaldehyde per 1° BX of the low-formaldehyde product, of between 0.2 wt. % hydroxyacetaldehyde per 1° BX of the low-formaldehyde product and 0.5 wt. % hydroxyacetaldehyde per 1° BX of the low-formaldehyde product, of between 0.3 wt. % hydroxyacetaldehyde per 1° BX of the low-formaldehyde product and 0.5 wt. % hydroxyacetaldehyde per 1° BX of the low-formaldehyde product, or the low-formaldehyde product may have a ratio of between 0.4 wt. % hydroxyacetaldehyde per 1° BX of the low-formaldehyde product and 0.5 wt. % hydroxyacetaldehyde per 1° BX of the low-formaldehyde product.

In certain embodiments, for example, the low-formaldehyde product may be a browning agent (for example a food browning agent). In certain embodiments, for example, the low-formaldehyde product may be a microwave browning agent (for example an agent for browning a food in a microwave oven). In certain embodiments, for example, the low-formaldehyde product may be a flavoring agent (for example a food flavoring agent). In certain embodiments, for example, the low-formaldehyde product may be used for chemicals, plastics, binders, solvents, and/or crosslinkers. In certain embodiments, for example, the low-formaldehyde product may be used to derive chemicals, plastics, binders, solvents, and/or crosslinkers. In certain embodiments, for example, the low-formaldehyde product may be further processed to yield chemicals, plastics, binders, solvents, and/or crosslinkers. In certain embodiments, for example, the low-formaldehyde product may a source for chemicals, plastics, binders, solvents, and/or crosslinkers. In certain embodiments, for example, the low-formaldehyde product may be rich in components for chemicals, plastics, binders, solvents, and/or crosslinkers.

C. In certain embodiments, for example, the pyrolyzing may occur at a temperature of between 400° C. and 600° C., for example the pyrolyzing may occur at a temperature of between 400° C. and 550° C., at a temperature of between 500° C. and 600° C., at a temperature of between 400° C. and 500° C., at a temperature of between 450° C. and 550° C., at a temperature of between 400° C. and 495° C., at a temperature of between 450° C. and 495° C., at a temperature of between 400° C. and 495° C., at a temperature of between 400° C. and 490° C., at a temperature of between 400° C. and 480° C., at a temperature of between 400° C. and 470° C., at a temperature of between 400° C. and 460° C., at a temperature of between 400° C. and 450° C., at a temperature of between 400° C. and 440° C., at a temperature of between 400° C. and 425° C., at a temperature of between 475° C. and 495° C., or the pyrolyzing may occur at a temperature of between 425° C. and 475° C. In certain embodiments, for example, the pyrolyzing may occur at a temperature of less than 600° C., for example the pyrolyzing may occur at a temperature of less than 575° C., at a temperature of less than 550° C., at a temperature of less than 525° C., at a temperature of less than 500° C., at a temperature of less than 495° C., at a temperature of less than 490° C., at a temperature of less than 480° C., at a temperature of less than 470° C., at a temperature of less than 460° C., at a temperature of less than 450° C., at a temperature of less than 440° C., or the pyrolyzing may occur at a temperature of less than 425° C.

D. In certain embodiments, for example, the biomass may be pyrolyzed in an upflow pyrolysis reactor. In certain embodiments, for example, the pyrolyzing may comprise introducing a low oxygen or oxygen-free fluidization gas to the upflow reactor. In certain embodiments, for example, the fluidization gas may be water-free. In certain embodiments, for example, the fluidization gas may be formaldehyde-free. In certain embodiments, for example, the fluidization gas may be a once-through fluidization gas. In certain embodiments, for example, the fluidization gas may not be recirculated or reused by the pyrolysis reactor. In certain embodiments, for example, the fluidization gas may be nitrogen gas. In certain embodiments, for example, the fluidization gas may be a by-product gas, resulting from the process. In certain embodiments, for example, the nitrogen gas may be provided from a cryogenic source. In certain embodiments, for example, the fluidization gas may be a combustion product flue gas. In certain embodiments, for example, the combustion product flue gas may be obtained from a unit operation in communication with the pyrolysis reactor. In certain embodiments, for example, the unit operation may be a heat transfer particle reheater.

E. In certain embodiments, for example, the low-formaldehyde product may be a liquid. In certain embodiments, for example, the low-formaldehyde product may be a condensate. In certain embodiments, for example, the low-formaldehyde product may be present in a separate liquid phase from the liquid quench media (or coolant). In certain embodiments, for example, the low-formaldehyde product may be a solid. In certain embodiments, for example, the low-formaldehyde product may be a gas.

F. In certain embodiments, for example, the condensing may be performed in a single stage condenser. In certain embodiments, for example, the condensing may be performed in a single pass condenser. In certain embodiments, for example, the condensing may be performed in a single stage, single pass condenser. In certain embodiments, for example, the condensing may be performed in a condenser that recirculates the nonaqueous quench media. In certain embodiments, for example, the condensing may be performed in a single stage, single pass condenser that recirculates the nonaqueous quench media (or coolant).

G. In certain embodiments, for example, the nonaqueous quench media may be a nonaqueous liquid coolant. In certain embodiments, for example, the nonaqueous liquid coolant may be water-immiscible. In certain embodiments, for example, a solubility of water in the nonaqueous liquid coolant at 25° C. may be less than 10000 ppm, for example a solubility of water in the nonaqueous liquid coolant at 25° C. may be less than 1000 ppm, less than 750 ppm, less than 500 ppm, less than 250 ppm, less than 100 ppm, less than 50 ppm, less than 25 ppm, less than 10 ppm, or a solubility of water in the nonaqueous liquid coolant at 25° C. may be less than 1 ppm. In certain embodiments, for example, a solubility of water in the nonaqueous liquid coolant at 25° C. may be between 1 ppm and 10000 ppm, for example a solubility of water in the nonaqueous liquid coolant at 25° C. may be between 1 ppm and 10 ppm, between 10 ppm and 100 ppm, between 100 ppm and 1000 ppm, or a solubility of water in the nonaqueous liquid coolant at 25° C. may be between 1000 ppm and 10000 ppm.

In certain embodiments, for example, a solubility of the nonaqueous liquid coolant in water at 25° C. may be less than 10000 ppm, for example a solubility of the nonaqueous liquid coolant in water at 25° C. may be less than 1000 ppm, less than 750 ppm, less than 500 ppm, less than 250 ppm, less than 100 ppm, less than 50 ppm, less than 25 ppm, less than 10 ppm, or a solubility of the nonaqueous liquid coolant in water at 25° C. may be less than 1 ppm. In certain embodiments, for example, a solubility of the nonaqueous liquid coolant in water at 25° C. may be between 1 ppm and 10000 ppm, for example a solubility of the nonaqueous liquid coolant in water at 25° C. may be between 1 ppm and 10 ppm, between 10 ppm and 100 ppm, between 100 ppm and 1000 ppm, or a solubility of the nonaqueous liquid coolant in water at 25° C. may be between 1000 ppm and 10000 ppm.

In certain embodiments, for example, the nonaqueous coolant may phase separate from water. In certain embodiments, for example, the nonaqueous coolant may phase separate from the low-formaldehyde product.

In certain embodiments, for example, a solubility of formaldehyde in the nonaqueous liquid coolant at 25° C. may be less than 10000 ppm, for example a solubility of formaldehyde in the nonaqueous liquid coolant at 25° C. may be less than 1000 ppm, less than 750 ppm, less than 500 ppm, less than 250 ppm, less than 100 ppm, less than 50 ppm, less than 25 ppm, less than 10 ppm, or a solubility of formaldehyde in the nonaqueous liquid coolant at 25° C. may be less than 1 ppm. In certain embodiments, for example, a solubility of formaldehyde in the nonaqueous liquid coolant at 25° C. may be between 1 ppm and 10000 ppm, for example a solubility of formaldehyde in the nonaqueous liquid coolant at 25° C. may be between 1 ppm and 10 ppm, between 10 ppm and 100 ppm, between 100 ppm and 1000 ppm, or a solubility of formaldehyde in the nonaqueous liquid coolant at 25° C. may be between 1000 ppm and 10000 ppm.

In certain embodiments, for example, a solubility of the nonaqueous liquid coolant in formaldehyde at 25° C. may be less than 10000 ppm, for example a solubility of the nonaqueous liquid coolant in formaldehyde at 25° C. may be less than 1000 ppm, less than 750 ppm, less than 500 ppm, less than 250 ppm, less than 100 ppm, less than 50 ppm, less than 25 ppm, less than 10 ppm, or a solubility of the nonaqueous liquid coolant in formaldehyde at 25° C. may be less than 1 ppm. In certain embodiments, for example, a solubility of the nonaqueous liquid coolant in formaldehyde at 25° C. may be between 1 ppm and 10000 ppm, for example a solubility of the nonaqueous liquid coolant in formaldehyde at 25° C. may be between 1 ppm and 10 ppm, between 10 ppm and 100 ppm, between 100 ppm and 1000 ppm, or a solubility of the nonaqueous liquid coolant in formaldehyde at 25° C. may be between 1000 ppm and 10000 ppm.

In certain embodiments, for example, the nonaqueous coolant may be an organic liquid. In certain embodiments, for example, the nonaqueous coolant may be dodecane. In certain embodiments, for example, the nonaqueous coolant may be a non-organic liquid.

H. In certain embodiments, for example, the separated at least a portion of the low-formaldehyde product may comprise at least 10 wt. % of the total vapor pyrolysis products, the separated at least a portion of the low-formaldehyde product may comprise at least 20 wt. % of the vapor pyrolysis products, at least 30 wt. % of the vapor pyrolysis products, at least 40 wt. % of the vapor pyrolysis products, at least 50 wt. % of the vapor pyrolysis products, at least 60 wt. % of the vapor pyrolysis products, at least 70 wt. % of the vapor pyrolysis products, at least 75 wt. % of the vapor pyrolysis products, at least 80 wt. % of the vapor pyrolysis products, at least 85 wt. % of the vapor pyrolysis products, the separated at least a portion of the low-formaldehyde product may comprise at least 90 wt. % of the vapor pyrolysis products.

In certain embodiments, for example, the separated at least a portion of the low-formaldehyde product may comprise at least 10 wt. % of the total gaseous pyrolysis products, the separated at least a portion of the low-formaldehyde product may comprise at least 20 wt. % of the gaseous pyrolysis products, at least 30 wt. % of the gaseous pyrolysis products, at least 40 wt. % of the gaseous pyrolysis products, at least 50 wt. % of the gaseous pyrolysis products, at least 60 wt. % of the gaseous pyrolysis products, at least 70 wt. % of the gaseous pyrolysis products, at least 75 wt. % of the gaseous pyrolysis products, at least 80 wt. % of the gaseous pyrolysis products, at least 85 wt. % of the gaseous pyrolysis products, the separated at least a portion of the low-formaldehyde product may comprise at least 90 wt. % of the gaseous pyrolysis products.

In certain embodiments, for example, the separated at least a portion of the low-formaldehyde product may comprise at least 10 wt. % of the biomass, the separated at least a portion of the low-formaldehyde product may comprise at least 20 wt. % of the biomass, at least 30 wt. % of the biomass, at least 40 wt. % of the biomass, at least 50 wt. % of the biomass, at least 60 wt. % of the biomass, at least 70 wt. % of the biomass, at least 75 wt. % of the biomass, at least 80 wt. % of the biomass, at least 85 wt. % of the biomass, the separated at least a portion of the low-formaldehyde product may comprise at least 90 wt. % of the biomass.

In certain embodiments, for example, the nonaqueous coolant and the at least a portion of the low-formaldehyde product may form a two-phase mixture prior to the separating. In certain embodiments, for example, the separating may comprise phase separating the at least a portion of the low-formaldehyde product from the nonaqueous liquid. In certain embodiments, for example, the separating may occur in a condenser. In certain embodiments, for example, the separating may occur in a settling tank.

I. In certain embodiments, for example, the method may further comprise: passing the low-formaldehyde product through an evaporator. In certain embodiments, for example, passing the low-formaldehyde product through the evaporator may reduce a formaldehyde concentration of the low-formaldehyde product by at least 5%, for example passing the low-formaldehyde product through the evaporator may reduce a formaldehyde concentration of the low-formaldehyde product by at least 10%, by at least 15%, by at least 20%, by at least 25%, by at least 30%, by at least 35%, by at least 40%, by at least 45%, by at least 50%, by at least 55%, by at least 60%, by at least 65%, or passing the low-formaldehyde product through the evaporator may reduce a formaldehyde concentration of the low-formaldehyde product by at least 75%. In certain embodiments, for example, passing the low-formaldehyde product through the evaporator may reduce a formaldehyde concentration of the low-formaldehyde product by between 5% and 50%, for example passing the low-formaldehyde product through the evaporator may reduce a formaldehyde concentration of the low-formaldehyde product by between 5% and 25%, or passing the low-formaldehyde product through the evaporator may reduce a formaldehyde concentration of the low-formaldehyde product by between 10% and 50%.

In certain embodiments, for example, the method may further comprise: passing the low-formaldehyde product through liquid-liquid extraction unit. In certain embodiments, for example, the method may further comprise: contacting the low-formaldehyde product with a liquid selected to extract formaldehyde from the low-formaldehyde product. In certain embodiments, for example, passing the low-formaldehyde product through the liquid-liquid extraction unit may reduce a formaldehyde concentration of the low-formaldehyde product by at least 5%, for example passing the low-formaldehyde product through the liquid-liquid extraction unit may reduce a formaldehyde concentration of the low-formaldehyde product by at least 10%, by at least 15%, by at least 20%, by at least 25%, by at least 30%, by at least 35%, by at least 40%, by at least 45%, by at least 50%, by at least 55%, by at least 60%, by at least 65%, or passing the low-formaldehyde product through the liquid-liquid extraction unit may reduce a formaldehyde concentration of the low-formaldehyde product by at least 75%. In certain embodiments, for example, passing the low-formaldehyde product through the liquid-liquid extraction unit may reduce a formaldehyde concentration of the low-formaldehyde product by between 5% and 50%, for example passing the low-formaldehyde product through the liquid-liquid extraction unit may reduce a formaldehyde concentration of the low-formaldehyde product by between 5% and 25%, or passing the low-formaldehyde product through the liquid-liquid extraction unit may reduce a formaldehyde concentration of the low-formaldehyde product by between 10% and 50%.

In certain embodiments, for example, the method may further comprise: contacting the low-formaldehyde product with a material selected to absorb and/or adsorb formaldehyde from the low-formaldehyde product. In certain embodiments, for example, the material may be a clay. In certain embodiments, for example, the method may further comprise: contacting the low-formaldehyde product with bentonite. In certain embodiments, for example, contacting the low-formaldehyde product with the material may reduce a formaldehyde concentration of the low-formaldehyde product by at least 5%, for example contacting the low-formaldehyde product with the material may reduce a formaldehyde concentration of the low-formaldehyde product by at least 10%, by at least 15%, by at least 20%, by at least 25%, by at least 30%, by at least 35%, by at least 40%, by at least 45%, by at least 50%, by at least 55%, by at least 60%, by at least 65%, or contacting the low-formaldehyde product with the material may reduce a formaldehyde concentration of the low-formaldehyde product by at least 75%. In certain embodiments, for example, contacting the low-formaldehyde product with the material may reduce a formaldehyde concentration of the low-formaldehyde product by between 5% and 50%, for example contacting the low-formaldehyde product with the material may reduce a formaldehyde concentration of the low-formaldehyde product by between 5% and 25%, or contacting the low-formaldehyde product with the material may reduce a formaldehyde concentration of the low-formaldehyde product by between 10% and 50%.

Certain embodiments may provide, for example, a method for producing a low-formaldehyde product (for example a hydroxyacetaldehyde-rich product and/or a food flavoring product and/or a food browning product) having a ratio of formaldehyde-to-hydroxyacetaldehyde of no more than 0.02 (w/w). In certain embodiments, for example, the method may comprise: pyrolyzing (for example by fast pyrolysis) one or more simple sugars (for example pyrolyzing glucose in an upflow reactor) to form gaseous pyrolysis products. In certain embodiments, for example, the method may comprise: condensing (for example in a single stage, single pass condenser) a portion of the gaseous pyrolysis products (for example at least 50 wt. % of the gaseous pyrolysis products) to form the low-formaldehyde product, comprising: contacting the gaseous pyrolysis products with a nonaqueous coolant (for example an organic solvent such as dodecane). In certain embodiments, for example, the method may comprise: separating at least a portion of the low-formaldehyde product from the nonaqueous coolant (for example separating a liquid phase comprising the low-formaldehyde product from a separate liquid phase comprising the nonaqueous coolant).

A. In certain embodiments, for example, the low-formaldehyde product may have a ratio of formaldehyde-to-hydroxyacetaldehyde of no more than 0.019 (w/w), for example the low-formaldehyde product may have a ratio of formaldehyde-to-hydroxyacetaldehyde of no more than 0.018 (w/w), of no more than 0.017 (w/w), of no more than 0.016 (w/w), of no more than 0.015 (w/w), of no more than 0.014 (w/w), of no more than 0.013 (w/w), of no more than 0.012 (w/w), of no more than 0.011 (w/w), of no more than 0.010 (w/w), of no more than 0.009 (w/w), of no more than 0.008 (w/w), of no more than 0.007 (w/w), of no more than 0.006 (w/w), of no more than 0.005 (w/w), of no more than 0.004 (w/w), of no more than 0.003 (w/w), of no more than 0.002 (w/w), or the low-formaldehyde product may have a ratio of formaldehyde-to-hydroxyacetaldehyde of no more than 0.001 (w/w). In certain embodiments, for example, the low-formaldehyde product may have a ratio of formaldehyde-to-hydroxyacetaldehyde of between 0.001 (w/w) and 0.02 (w/w), for example a ratio of formaldehyde-to-hydroxyacetaldehyde of between 0.005 (w/w) and 0.02 (w/w), of between 0.01 (w/w) and 0.02 (w/w), of between 0.015 (w/w) and 0.02 (w/w), of between 0.01 (w/w) and 0.015 (w/w), of between 0.015 (w/w) and 0.018 (w/w), or the low-formaldehyde product may have a ratio of formaldehyde-to-hydroxyacetaldehyde of between 0.016 (w/w) and 0.019 (w/w).

In certain embodiments, for example, the low-formaldehyde product may have a ratio of no more than 500 ppm formaldehyde per 1° BX of the low-formaldehyde product, for example the low-formaldehyde product may have a ratio of no more than 400 ppm formaldehyde per 1° BX of the low-formaldehyde product, a ratio of no more than 300 ppm formaldehyde per 1° BX of the low-formaldehyde product, a ratio of no more than 200 ppm formaldehyde per 1° BX of the low-formaldehyde product, a ratio of no more than 100 ppm formaldehyde per 1° BX of the low-formaldehyde product, a ratio of no more than 90 ppm formaldehyde per 1° BX of the low-formaldehyde product, a ratio of no more than 80 ppm formaldehyde per 1° BX of the low-formaldehyde product, a ratio of no more than 70 ppm formaldehyde per 1° BX of the low-formaldehyde product, a ratio of no more than 60 ppm formaldehyde per 1° BX of the low-formaldehyde product, a ratio of no more than 50 ppm formaldehyde per 1° BX of the low-formaldehyde product, a ratio of no more than 40 ppm formaldehyde per 1° BX of the low-formaldehyde product, a ratio of no more than 30 ppm formaldehyde per 1° BX of the low-formaldehyde product, a ratio of no more than 20 ppm formaldehyde per 1° BX of the low-formaldehyde product, a ratio of no more than 10 ppm formaldehyde per 1° BX of the low-formaldehyde product, or the low-formaldehyde product may have a ratio of no more than 5 ppm formaldehyde per 1° BX of the low-formaldehyde product. In certain embodiments, for example, the low-formaldehyde product may have a ratio of between 10 ppm formaldehyde per 1° BX of the low-formaldehyde product and 500 ppm formaldehyde per 1° BX of the low-formaldehyde product, for example the low-formaldehyde product may have a ratio of between 10 ppm formaldehyde per 1° BX of the low-formaldehyde product and 400 ppm formaldehyde per 1° BX of the low-formaldehyde product, of between 10 ppm formaldehyde per 1° BX of the low-formaldehyde product and 300 ppm formaldehyde per 1° BX of the low-formaldehyde product, of between 10 ppm formaldehyde per 1° BX of the low-formaldehyde product and 200 ppm formaldehyde per 1° BX of the low-formaldehyde product, of between 10 ppm formaldehyde per 1° BX of the low-formaldehyde product and 100 ppm formaldehyde per 1° BX of the low-formaldehyde product, of between 20 ppm formaldehyde per 1° BX of the low-formaldehyde product and 75 ppm formaldehyde per 1° BX of the low-formaldehyde product, of between 10 ppm formaldehyde per 1° BX of the low-formaldehyde product and 75 ppm formaldehyde per 1° BX of the low-formaldehyde product, of between 20 ppm formaldehyde per 1° BX of the low-formaldehyde product and 75 ppm formaldehyde per 1° BX of the low-formaldehyde product, of between 10 ppm formaldehyde per 1° BX of the low-formaldehyde product and 50 ppm formaldehyde per 1° BX of the low-formaldehyde product, of between 20 ppm formaldehyde per 1° BX of the low-formaldehyde product and 50 ppm formaldehyde per 1° BX of the low-formaldehyde product, of between 25 ppm formaldehyde per 1° BX of the low-formaldehyde product and 40 ppm formaldehyde per 1° BX of the low-formaldehyde product, of between 50 ppm formaldehyde per 1° BX of the low-formaldehyde product and 150 ppm formaldehyde per 1° BX of the low-formaldehyde product, of between 50 ppm formaldehyde per 1° BX of the low-formaldehyde product and 125 ppm formaldehyde per 1° BX of the low-formaldehyde product, of between 60 ppm formaldehyde per 1° BX of the low-formaldehyde product and 100 ppm formaldehyde per 1° BX of the low-formaldehyde product, of between 50 ppm formaldehyde per 1° BX of the low-formaldehyde product and 90 ppm formaldehyde per 1° BX of the low-formaldehyde product, of between 70 ppm formaldehyde per 1° BX of the low-formaldehyde product and 100 ppm formaldehyde per 1° BX of the low-formaldehyde product, or the low-formaldehyde product may have a ratio of between 75 ppm formaldehyde per 1° BX of the low-formaldehyde product and 95 ppm formaldehyde per 1° BX of the low-formaldehyde product.

In certain embodiments, for example, the low-formaldehyde product may have a ratio of at least 0.01 wt. % hydroxyacetaldehyde per 1° BX of the low-formaldehyde product, for example, the low-formaldehyde product may have a ratio of at least 0.05 wt. % hydroxyacetaldehyde per 1° BX of the low-formaldehyde product, of at least 0.1 wt. % hydroxyacetaldehyde per 1° BX of the low-formaldehyde product, of at least 0.2 wt. % hydroxyacetaldehyde per 1° BX of the low-formaldehyde product, of at least 0.3 wt. % hydroxyacetaldehyde per 1° BX of the low-formaldehyde product, of at least 0.35 wt. % hydroxyacetaldehyde per 1° BX of the low-formaldehyde product, of at least 0.4 wt. % hydroxyacetaldehyde per 1° BX of the low-formaldehyde product, of at least 0.45 wt. % hydroxyacetaldehyde per 1° BX of the low-formaldehyde product, or the low-formaldehyde product may have a ratio of at least 0.5 wt. % hydroxyacetaldehyde per 1° BX of the low-formaldehyde product. In certain embodiments, for example, the low-formaldehyde product may have a ratio of between 0.05 wt. % hydroxyacetaldehyde per 1° BX of the low-formaldehyde product and 0.5 wt. % hydroxyacetaldehyde per 1° BX of the low-formaldehyde product, for example the low-formaldehyde product may have a ratio of between 0.1 wt. % hydroxyacetaldehyde per 1° BX of the low-formaldehyde product and 0.5 wt. % hydroxyacetaldehyde per 1° BX of the low-formaldehyde product, of between 0.2 wt. % hydroxyacetaldehyde per 1° BX of the low-formaldehyde product and 0.5 wt. % hydroxyacetaldehyde per 1° BX of the low-formaldehyde product, of between 0.3 wt. % hydroxyacetaldehyde per 1° BX of the low-formaldehyde product and 0.5 wt. % hydroxyacetaldehyde per 1° BX of the low-formaldehyde product, or the low-formaldehyde product may have a ratio of between 0.4 wt. % hydroxyacetaldehyde per 1° BX of the low-formaldehyde product and 0.5 wt. % hydroxyacetaldehyde per 1° BX of the low-formaldehyde product.

In certain embodiments, for example, the low-formaldehyde product may be a browning agent (for example a food browning agent such as the water soluble, aqueous browning agent derived from dextrose sold under the trade name MAILLOSE). In certain embodiments, for example, the low-formaldehyde product may be a microwave browning agent (for example an agent for browning a food in a microwave oven). In certain embodiments, for example, the low-formaldehyde product may be a flavoring agent (for example a food flavoring agent).

B. In certain embodiments, for example, the pyrolyzing may occur at a temperature of between 400° C. and 600° C., for example the pyrolyzing may occur at a temperature of between 400° C. and 550° C., at a temperature of between 500° C. and 600° C., at a temperature of between 400° C. and 500° C., at a temperature of between 450° C. and 550° C., at a temperature of between 400° C. and 495° C., at a temperature of between 450° C. and 495° C., at a temperature of between 400° C. and 495° C., at a temperature of between 400° C. and 490° C., at a temperature of between 400° C. and 480° C., at a temperature of between 400° C. and 470° C., at a temperature of between 400° C. and 460° C., at a temperature of between 400° C. and 450° C., at a temperature of between 400° C. and 440° C., at a temperature of between 400° C. and 425° C., at a temperature of between 475° C. and 495° C., or the pyrolyzing may occur at a temperature of between 425° C. and 475° C. In certain embodiments, for example, the pyrolyzing may occur at a temperature of less than 600° C., for example the pyrolyzing may occur at a temperature of less than 575° C., at a temperature of less than 550° C., at a temperature of less than 525° C., at a temperature of less than 500° C., at a temperature of less than 495° C., at a temperature of less than 490° C., at a temperature of less than 480° C., at a temperature of less than 470° C., at a temperature of less than 460° C., at a temperature of less than 450° C., at a temperature of less than 440° C., or the pyrolyzing may occur at a temperature of less than 425° C.

C. In certain embodiments, for example, the one or more simple sugars may be pyrolyzed in any of the pyrolysis reactors disclosed in the INCORPORATED REFERENCES. In certain embodiments, for example, an upflow pyrolysis reactor may be employed. In certain embodiments, for example, the pyrolyzing may comprise introducing a low oxygen or oxygen-free fluidization gas to the upflow reactor. In certain embodiments, for example, the fluidization gas may be water-free. In certain embodiments, for example, the fluidization gas may be formaldehyde-free. In certain embodiments, for example, the fluidization gas may be a once-through fluidization gas. In certain embodiments, for example, the fluidization gas may not be recirculated or reused by the pyrolysis reactor. In certain embodiments, for example, the fluidization gas may be nitrogen gas. In certain embodiments, for example, the nitrogen gas may be provided from a cryogenic source. In certain embodiments, for example, the fluidization gas may be a combustion product flue gas. In certain embodiments, for example, the combustion product flue gas may be obtained from a unit operation in communication with the pyrolysis reactor. In certain embodiments, for example, the unit operation may be a heat transfer particle reheater.

D. In certain embodiments, for example, the one or more simple sugars may comprise one or more of the simple sugars disclosed herein and/or in the INCORPORATED REFERENCES. In certain embodiments, for example, the one or more simple sugars may comprise glucose. In certain embodiments, for example, the one or more single sugars may be glucose. In certain embodiments, for example, the one or more simple sugars may comprise one or more food grade sugars. In certain embodiments, for example, the one or more simple sugars may be an impure mixture of different sugars. In certain embodiments, for example, the one or more simple sugars may be present in a complex biomass (for example in a potato, a sugar beet, or one or more of the complex biomass materials disclosed herein and/or in the INCORPORATED

REFERENCES

In certain embodiments, for example, the one or more simple sugars may be provided in a solution. In certain embodiments, for example, the solution may have a BRIX value of at least 10° BX, for example the solution may have a BRIX value of at least 20° BX, of at least 30° BX, of at least 40° BX, of at least 50° BX, of at least 60° BX, of at least 65° BX, of at least 70° BX, of at least 80° BX, or the solution may have a BRIX value of at least 90° BX. In certain embodiments, for example, the solution may have a BRIX value of between 40° BX and 80° BX, for example the solution may have a BRIX value of between 40° BX and 75° BX, of between 40° BX and 70° BX, of between 50° BX and 70° BX, or the solution may have a BRIX value of between 60° BX and 75° BX.

In certain embodiments, for example, the one or more simple sugars may be provided in a particulate solid. In certain embodiments, for example, the particulate solid may be provided in a fluidization gas. In certain embodiments, for example, the one or more simple sugars may be provided in a liquid. In certain embodiments, for example, the one or more simple sugars may be provided in a syrup. In certain embodiments, for example, the one or more simple sugars may be provided in a suspension (for example particles containing the one or more simple sugars suspended in a liquid).

E. In certain embodiments, for example, the low-formaldehyde product may be a liquid. In certain embodiments, for example, the low-formaldehyde product may be a condensate. In certain embodiments, for example, the low-formaldehyde product may be present in a separate liquid phase from the liquid coolant. In certain embodiments, for example, the low-formaldehyde product may be a solid. In certain embodiments, for example, the low-formaldehyde product may be a gas.

F. In certain embodiments, for example, the condensing may be performed in one or a combination of the applicable unit operations disclosed herein and/or in the INCORPORATED REFERENCES. In certain embodiments, for example, the condensing may be performed in a single stage condenser. In certain embodiments, for example, the condensing may be performed in a single pass condenser. In certain embodiments, for example, the condensing may be performed in a single stage, single pass condenser. In certain embodiments, for example, the condensing may be performed in a condenser that recirculates the nonaqueous coolant. In certain embodiments, for example, the condensing may be performed in a single stage, single pass condenser that recirculates the nonaqueous coolant.

G. In certain embodiments, for example, the nonaqueous coolant may be a nonaqueous liquid coolant. In certain embodiments, for example, the nonaqueous liquid coolant may be water-immiscible. In certain embodiments, for example, a solubility of water in the nonaqueous liquid coolant at 25° C. may be less than 10000 ppm, for example a solubility of water in the nonaqueous liquid coolant at 25° C. may be less than 1000 ppm, less than 750 ppm, less than 500 ppm, less than 250 ppm, less than 100 ppm, less than 50 ppm, less than 25 ppm, less than 10 ppm, or a solubility of water in the nonaqueous liquid coolant at 25° C. may be less than 1 ppm. In certain embodiments, for example, a solubility of water in the nonaqueous liquid coolant at 25° C. may be between 1 ppm and 10000 ppm, for example a solubility of water in the nonaqueous liquid coolant at 25° C. may be between 1 ppm and 10 ppm, between 10 ppm and 100 ppm, between 100 ppm and 1000 ppm, or a solubility of water in the nonaqueous liquid coolant at 25° C. may be between 1000 ppm and 10000 ppm.

In certain embodiments, for example, a solubility of the nonaqueous liquid coolant in water at 25° C. may be less than 10000 ppm, for example a solubility of the nonaqueous liquid coolant in water at 25° C. may be less than 1000 ppm, less than 750 ppm, less than 500 ppm, less than 250 ppm, less than 100 ppm, less than 50 ppm, less than 25 ppm, less than 10 ppm, or a solubility of the nonaqueous liquid coolant in water at 25° C. may be less than 1 ppm. In certain embodiments, for example, a solubility of the nonaqueous liquid coolant in water at 25° C. may be between 1 ppm and 10000 ppm, for example a solubility of the nonaqueous liquid coolant in water at 25° C. may be between 1 ppm and 10 ppm, between 10 ppm and 100 ppm, between 100 ppm and 1000 ppm, or a solubility of the nonaqueous liquid coolant in water at 25° C. may be between 1000 ppm and 10000 ppm.

In certain embodiments, for example, the nonaqueous coolant may phase separate (for example naturally settle and phase separate) from water. In certain embodiments, for example, the nonaqueous coolant ay phase separate from the low-formaldehyde product.

In certain embodiments, for example, a solubility of formaldehyde in the nonaqueous liquid coolant at 25° C. may be less than 10000 ppm, for example a solubility of formaldehyde in the nonaqueous liquid coolant at 25° C. may be less than 1000 ppm, less than 750 ppm, less than 500 ppm, less than 250 ppm, less than 100 ppm, less than 50 ppm, less than 25 ppm, less than 10 ppm, or a solubility of formaldehyde in the nonaqueous liquid coolant at 25° C. may be less than 1 ppm. In certain embodiments, for example, a solubility of formaldehyde in the nonaqueous liquid coolant at 25° C. may be between 1 ppm and 10000 ppm, for example a solubility of formaldehyde in the nonaqueous liquid coolant at 25° C. may be between 1 ppm and 10 ppm, between 10 ppm and 100 ppm, between 100 ppm and 1000 ppm, or a solubility of formaldehyde in the nonaqueous liquid coolant at 25° C. may be between 1000 ppm and 10000 ppm.

In certain embodiments, for example, a solubility of the nonaqueous liquid coolant in formaldehyde at 25° C. may be less than 10000 ppm, for example a solubility of the nonaqueous liquid coolant in formaldehyde at 25° C. may be less than 1000 ppm, less than 750 ppm, less than 500 ppm, less than 250 ppm, less than 100 ppm, less than 50 ppm, less than 25 ppm, less than 10 ppm, or a solubility of the nonaqueous liquid coolant in formaldehyde at 25° C. may be less than 1 ppm. In certain embodiments, for example, a solubility of the nonaqueous liquid coolant in formaldehyde at 25° C. may be between 1 ppm and 10000 ppm, for example a solubility of the nonaqueous liquid coolant in formaldehyde at 25° C. may be between 1 ppm and 10 ppm, between 10 ppm and 100 ppm, between 100 ppm and 1000 ppm, or a solubility of the nonaqueous liquid coolant in formaldehyde at 25° C. may be between 1000 ppm and 10000 ppm.

In certain embodiments, for example, the nonaqueous coolant may be an organic solvent. In certain embodiments, for example, the nonaqueous coolant may be dodecane.

H. In certain embodiments, for example, the separated at least a portion of the low-formaldehyde product may comprise at least 10 wt. % of the gaseous pyrolysis products, the separated at least a portion of the low-formaldehyde product may comprise at least 20 wt. % of the gaseous pyrolysis products, at least 30 wt. % of the gaseous pyrolysis products, at least 40 wt. % of the gaseous pyrolysis products, at least 50 wt. % of the gaseous pyrolysis products, at least 60 wt. % of the gaseous pyrolysis products, at least 70 wt. % of the gaseous pyrolysis products, at least 75 wt. % of the gaseous pyrolysis products, at least 80 wt. % of the gaseous pyrolysis products, at least 85 wt. % of the gaseous pyrolysis products, the separated at least a portion of the low-formaldehyde product may comprise at least 90 wt. % of the gaseous pyrolysis products.

In certain embodiments, for example, the separated at least a portion of the low-formaldehyde product may comprise at least 10 wt. % of the one or more simple sugars, the separated at least a portion of the low-formaldehyde product may comprise at least 20 wt. % of the one or more simple sugars, at least 30 wt. % of the one or more simple sugars, at least 40 wt. % of the one or more simple sugars, at least 50 wt. % of the one or more simple sugars, at least 60 wt. % of the one or more simple sugars, at least 70 wt. % of the one or more simple sugars, at least 75 wt. % of the one or more simple sugars, at least 80 wt. % of the one or more simple sugars, at least 85 wt. % of the one or more simple sugars, the separated at least a portion of the low-formaldehyde product may comprise at least 90 wt. % of the one or more simple sugars.

In certain embodiments, for example, the nonaqueous coolant and the at least a portion of the low-formaldehyde product may form a two-phase mixture prior to the separating. In certain embodiments, for example, the separating may comprise phase separating the at least a portion of the low-formaldehyde product from the nonaqueous liquid. In certain embodiments, for example, the separating may occur in a condenser. In certain embodiments, for example, the separating may occur in a settling tank.

I. In certain embodiments, for example, the method may further comprise: passing the low-formaldehyde product through an evaporator, for example, but not limited to wipe-film evaporators, thin film evaporators, plate and frame evaporators, falling film evaporators, climbing film evaporators, multi-effect evaporators, natural/forced circulation evaporators and/or combinations and hybrids thereof (and any of the evaporators disclosed in the INCORPORATED REFERENCES). In certain embodiments, for example, passing the low-formaldehyde product through the evaporator may reduce a formaldehyde concentration of the low-formaldehyde product by at least 5%, for example passing the low-formaldehyde product through the evaporator may reduce a formaldehyde concentration of the low-formaldehyde product by at least 10%, by at least 15%, by at least 20%, by at least 25%, by at least 30%, by at least 35%, by at least 40%, by at least 45%, by at least 50%, by at least 55%, by at least 60%, by at least 65%, or passing the low-formaldehyde product through the evaporator may reduce a formaldehyde concentration of the low-formaldehyde product by at least 75%. In certain embodiments, for example, passing the low-formaldehyde product through the evaporator may reduce a formaldehyde concentration of the low-formaldehyde product by between 5% and 50%, for example passing the low-formaldehyde product through the evaporator may reduce a formaldehyde concentration of the low-formaldehyde product by between 5% and 25%, or passing the low-formaldehyde product through the evaporator may reduce a formaldehyde concentration of the low-formaldehyde product by between 10% and 50%.

In certain embodiments, for example, the method may further comprise: passing the low-formaldehyde product through liquid-liquid extraction unit. In certain embodiments, for example, the method may further comprise: contacting the low-formaldehyde product with a liquid selected to extract formaldehyde from the low-formaldehyde product. In certain embodiments, for example, passing the low-formaldehyde product through the liquid-liquid extraction unit may reduce a formaldehyde concentration of the low-formaldehyde product by at least 5%, for example passing the low-formaldehyde product through the liquid-liquid extraction unit may reduce a formaldehyde concentration of the low-formaldehyde product by at least 10%, by at least 15%, by at least 20%, by at least 25%, by at least 30%, by at least 35%, by at least 40%, by at least 45%, by at least 50%, by at least 55%, by at least 60%, by at least 65%, or passing the low-formaldehyde product through the liquid-liquid extraction unit may reduce a formaldehyde concentration of the low-formaldehyde product by at least 75%. In certain embodiments, for example, passing the low-formaldehyde product through the liquid-liquid extraction unit may reduce a formaldehyde concentration of the low-formaldehyde product by between 5% and 50%, for example passing the low-formaldehyde product through the liquid-liquid extraction unit may reduce a formaldehyde concentration of the low-formaldehyde product by between 5% and 25%, or passing the low-formaldehyde product through the liquid-liquid extraction unit may reduce a formaldehyde concentration of the low-formaldehyde product by between 10% and 50%.

In certain embodiments, for example, the method may further comprise: contacting the low-formaldehyde product with a material selected to absorb formaldehyde from the low-formaldehyde product. In certain embodiments, for example, the material may be a clay. In certain embodiments, for example, the method may further comprise: contacting the low-formaldehyde product with bentonite. In certain embodiments, for example, contacting the low-formaldehyde product with the material may reduce a formaldehyde concentration of the low-formaldehyde product by at least 5%, for example contacting the low-formaldehyde product with the material may reduce a formaldehyde concentration of the low-formaldehyde product by at least 10%, by at least 15%, by at least 20%, by at least 25%, by at least 30%, by at least 35%, by at least 40%, by at least 45%, by at least 50%, by at least 55%, by at least 60%, by at least 65%, or contacting the low-formaldehyde product with the material may reduce a formaldehyde concentration of the low-formaldehyde product by at least 75%. In certain embodiments, for example, contacting the low-formaldehyde product with the material may reduce a formaldehyde concentration of the low-formaldehyde product by between 5% and 50%, for example contacting the low-formaldehyde product with the material may reduce a formaldehyde concentration of the low-formaldehyde product by between 5% and 25%, or contacting the low-formaldehyde product with the material may reduce a formaldehyde concentration of the low-formaldehyde product by between 10% and 50%.

Certain embodiments may provide, for example, a method for producing a low-formaldehyde product having a ratio of formaldehyde-to-hydroxyacetaldehyde of no more than 0.02 (w/w). In certain embodiments, for example, the method may comprise: pyrolyzing one or more simple sugars to form gaseous pyrolysis products. In certain embodiments, for example, the method may comprise: condensing a portion of the gaseous pyrolysis products to form the low-formaldehyde product, comprising: contacting the gaseous pyrolysis products with a liquid coolant having a formaldehyde solubility at 25° C. of less than 100 ppm formaldehyde (for example a solubility of less than 50 ppm, less than 10 ppm, or less than 1 ppm) in the liquid coolant. In certain embodiments, for example, the method may comprise: separating at least a portion of the low-formaldehyde product from the liquid coolant.

A. In certain embodiments, for example, a solubility of formaldehyde in the liquid coolant at 25° C. may be less than 90 ppm, for example a solubility of formaldehyde in the liquid coolant at 25° C. may be less than 80 ppm, less than 70 ppm, less than 60 ppm, less than 50 ppm, less than 40 ppm, less than 30 ppm, less than 20 ppm, less than 10 ppm, less than 5 ppm, or a solubility of formaldehyde in the liquid coolant at 25° C. may be less than 1 ppm. In certain embodiments, for example, a solubility of formaldehyde in the liquid coolant at 25° C. may be between 1 ppm and 100 ppm, for example a solubility of formaldehyde in the liquid coolant at 25° C. may be between 1 ppm and 90 ppm, between 10 ppm and 100 ppm, between 10 ppm and 50 ppm, or a solubility of formaldehyde in the liquid coolant at 25° C. may be between 1 ppm and 25 ppm.

In certain embodiments, for example, a solubility of formaldehyde in the liquid coolant at a temperature of the condensing may be less than 100 ppm, for example a solubility of formaldehyde in the liquid coolant at a temperature of the condensing may be less than 80 ppm, less than 70 ppm, less than 60 ppm, less than 50 ppm, less than 40 ppm, less than 30 ppm, less than 20 ppm, less than 10 ppm, less than 5 ppm, or a solubility of formaldehyde in the liquid coolant at a temperature of the condensing may be less than 1 ppm. In certain embodiments, for example, a solubility of formaldehyde in the liquid coolant at a temperature of the condensing may be between 1 ppm and 100 ppm, for example a solubility of formaldehyde in the liquid coolant at a temperature of the condensing may be between 1 ppm and 90 ppm, between 10 ppm and 100 ppm, between 10 ppm and 50 ppm, or a solubility of formaldehyde in the liquid coolant at a temperature of the condensing may be between 1 ppm and 25 ppm. In certain embodiments, for example, the temperature of the condensing may be less than 80° C., for example the temperature of the condensing may be less than 70° C., less than 65° C., less than 60° C., less than 55° C., less than 50° C., less than 45° C., less than 40° C., less than 35° C., less than 30° C., less than 25° C., less than 20° C., less than 15° C., or the temperature of the condensing may be less than 10° C. In certain embodiments, for example, the temperature of the condensing may be between 10° C. and 80° C., for example the temperature of the condensing may be between 20° C. and 60° C., between 30° C. and 60° C., between 25° C. and 55° C., between 30° C. and 60° C., or the temperature of the condensing may be between 30° C. and 55° C.

In certain embodiments, for example, a solubility of formaldehyde in the liquid coolant at a temperature of the separating may be less than 90 ppm, for example a solubility of formaldehyde in the liquid coolant at a temperature of the separating may be less than 80 ppm, less than 70 ppm, less than 60 ppm, less than 50 ppm, less than 40 ppm, less than 30 ppm, less than 20 ppm, less than 10 ppm, less than 5 ppm, or a solubility of formaldehyde in the liquid coolant at a temperature of the separating may be less than 1 ppm. In certain embodiments, for example, a solubility of formaldehyde in the liquid coolant at a temperature of the separating may be between 1 ppm and 100 ppm, for example a solubility of formaldehyde in the liquid coolant at a temperature of the separating may be between 1 ppm and 90 ppm, between 10 ppm and 100 ppm, between 10 ppm and 50 ppm, or a solubility of formaldehyde in the liquid coolant at a temperature of the separating may be between 1 ppm and 25 ppm. In certain embodiments, for example, the temperature of the separating may be less than 80° C., for example the temperature of the separating may be less than 70° C., less than 65° C., less than 60° C., less than 55° C., less than 50° C., less than 45° C., less than 40° C., less than 35° C., less than 30° C., less than 25° C., less than 20° C., less than 15° C., or the temperature of the separating may be less than 10° C. In certain embodiments, for example, the temperature of the separating may be between 10° C. and 80° C., for example the temperature of the separating may be between 20° C. and 60° C., between 30° C. and 60° C., between 25° C. and 55° C., between 30° C. and 60° C., or the temperature of the separating may be between 30° C. and 55° C.

In certain embodiments, for example, a solubility of water in the liquid coolant at 25° C. may be less than 10000 ppm, for example a solubility of water in the liquid coolant at 25° C. may be less than 1000 ppm, less than 750 ppm, less than 500 ppm, less than 250 ppm, less than 100 ppm, less than 50 ppm, less than 25 ppm, less than 10 ppm, or a solubility of water in the liquid coolant at 25° C. may be less than 1 ppm. In certain embodiments, for example, a solubility of water in the liquid coolant at 25° C. may be between 1 ppm and 10000 ppm, for example a solubility of water in the liquid coolant at 25° C. may be between 1 ppm and 10 ppm, between 10 ppm and 100 ppm, between 100 ppm and 1000 ppm, or a solubility of water in the liquid coolant at 25° C. may be between 1000 ppm and 10000 ppm.

Certain embodiments may provide, for example, a method for producing a low-formaldehyde product having a ratio of formaldehyde-to-hydroxyacetaldehyde of no more than 0.02 (w/w). In certain embodiments, for example, the method may comprise: pyrolyzing one or more simple sugars to form gaseous pyrolysis products. In certain embodiments, for example, the method may comprise: condensing a portion of the gaseous pyrolysis products to form the low-formaldehyde product, comprising: contacting the gaseous pyrolysis products with a liquid coolant having a water solubility at 25° C. of less than 100 ppm (for example a solubility of less than 50 ppm, less than 10 ppm, or less than 1 ppm) water in the liquid coolant. In certain embodiments, for example, the method may comprise: separating at least a portion of the low-formaldehyde product from the liquid coolant.

A. In certain embodiments, for example, a solubility of water in the liquid coolant at 25° C. may be less than 90 ppm, for example a solubility of water in the liquid coolant at 25° C. may be less than 80 ppm, less than 70 ppm, less than 60 ppm, less than 50 ppm, less than 40 ppm, less than 30 ppm, less than 20 ppm, less than 10 ppm, less than 5 ppm, or a solubility of water in the liquid coolant at 25° C. may be less than 1 ppm. In certain embodiments, for example, a solubility of water in the liquid coolant at 25° C. may be between 1 ppm and 100 ppm, for example a solubility of water in the liquid coolant at 25° C. may be between 1 ppm and 90 ppm, between 10 ppm and 100 ppm, between 10 ppm and 50 ppm, or a solubility of water in the liquid coolant at 25° C. may be between 1 ppm and 25 ppm.

In certain embodiments, for example, a solubility of water in the liquid coolant at a temperature of the condensing may be less than 100 ppm, for example a solubility of water in the liquid coolant at a temperature of the condensing may be less than 80 ppm, less than 70 ppm, less than 60 ppm, less than 50 ppm, less than 40 ppm, less than 30 ppm, less than 20 ppm, less than 10 ppm, less than 5 ppm, or a solubility of water in the liquid coolant at a temperature of the condensing may be less than 1 ppm. In certain embodiments, for example, a solubility of water in the liquid coolant at a temperature of the condensing may be between 1 ppm and 100 ppm, for example a solubility of water in the liquid coolant at a temperature of the condensing may be between 1 ppm and 90 ppm, between 10 ppm and 100 ppm, between 10 ppm and 50 ppm, or a solubility of water in the liquid coolant at a temperature of the condensing may be between 1 ppm and 25 ppm. In certain embodiments, for example, the temperature of the condensing may be less than 80° C., for example the temperature of the condensing may be less than 70° C., less than 65° C., less than 60° C., less than 55° C., less than 50° C., less than 45° C., less than 40° C., less than 35° C., less than 30° C., less than 25° C., less than 20° C., less than 15° C., or the temperature of the condensing may be less than 10° C. In certain embodiments, for example, the temperature of the condensing may be between 10° C. and 80° C., for example the temperature of the condensing may be between 20° C. and 60° C., between 30° C. and 60° C., between 25° C. and 55° C., between 30° C. and 60° C., or the temperature of the condensing may be between 30° C. and 55° C.

In certain embodiments, for example, a solubility of water in the liquid coolant at a temperature of the separating may be less than 90 ppm, for example a solubility of water in the liquid coolant at a temperature of the separating may be less than 80 ppm, less than 70 ppm, less than 60 ppm, less than 50 ppm, less than 40 ppm, less than 30 ppm, less than 20 ppm, less than 10 ppm, less than 5 ppm, or a solubility of water in the liquid coolant at a temperature of the separating may be less than 1 ppm. In certain embodiments, for example, a solubility of water in the liquid coolant at a temperature of the separating may be between 1 ppm and 100 ppm, for example a solubility of water in the liquid coolant at a temperature of the separating may be between 1 ppm and 90 ppm, between 10 ppm and 100 ppm, between 10 ppm and 50 ppm, or a solubility of water in the liquid coolant at a temperature of the separating may be between 1 ppm and 25 ppm. In certain embodiments, for example, the temperature of the separating may be less than 80° C., for example the temperature of the separating may be less than 70° C., less than 65° C., less than 60° C., less than 55° C., less than 50° C., less than 45° C., less than 40° C., less than 35° C., less than 30° C., less than 25° C., less than 20° C., less than 15° C., or the temperature of the separating may be less than 10° C. In certain embodiments, for example, the temperature of the separating may be between 10° C. and 80° C., for example the temperature of the separating may be between 20° C. and 60° C., between 30° C. and 60° C., between 25° C. and 55° C., between 30° C. and 60° C., or the temperature of the separating may be between 30° C. and 55° C.

In certain embodiments, for example, a solubility of formaldehyde in the liquid coolant at 25° C. may be less than 10000 ppm, for example a solubility of formaldehyde in the liquid coolant at 25° C. may be less than 1000 ppm, less than 750 ppm, less than 500 ppm, less than 250 ppm, less than 100 ppm, less than 50 ppm, less than 25 ppm, less than 10 ppm, or a solubility of formaldehyde in the liquid coolant at 25° C. may be less than 1 ppm. In certain embodiments, for example, a solubility of formaldehyde in the liquid coolant at 25° C. may be between 1 ppm and 10000 ppm, for example a solubility of formaldehyde in the liquid coolant at 25° C. may be between 1 ppm and 10 ppm, between 10 ppm and 100 ppm, between 100 ppm and 1000 ppm, or a solubility of formaldehyde in the liquid coolant at 25° C. may be between 1000 ppm and 10000 ppm.

Certain embodiments may provide, for example, a method for producing a low-formaldehyde liquid product having a ratio of no more than 150 ppm formaldehyde per 1° BX of the low-formaldehyde liquid product. In certain embodiments, for example, the method may comprise: pyrolyzing one or more biomass components to form gaseous pyrolysis products. In certain embodiments, for example, the method may comprise: introducing the gaseous pyrolysis products into a separation unit (for example one of the separation units disclosed in the INCORPORATED REFERENCES). In certain embodiments, for example, the method may comprise: recirculated a liquid coolant having a water solubility at 25° C. of less than 100 ppm water from an outlet of the separation unit to an inlet of the separation unit. In certain embodiments, for example, the method may comprise: recovering the liquid product comprising at least 50 wt. % of the gaseous pyrolysis products from the separation unit.

Certain embodiments may provide, for example, a method for producing a low-formaldehyde liquid product having a ratio of no more than 150 ppm formaldehyde per 1° BX of the low-formaldehyde liquid product. In certain embodiments, for example, the method may comprise: pyrolyzing one or more biomass components to form gaseous pyrolysis products. In certain embodiments, for example, the method may comprise: condensing a portion of the gaseous pyrolysis products to form the low-formaldehyde product, comprising contacting the gaseous pyrolysis products with a liquid coolant that is immiscible with the liquid product. In certain embodiments, for example, the method may comprise: physically separating the liquid product from the liquid coolant.

A. In certain embodiments, for example, the liquid product and the liquid coolant may settle into separate phases in a vessel where the condensing occurs. In certain embodiments, for example, the liquid product may be recovered as a separate phase from the liquid coolant.

B. In certain embodiments, for example, the liquid coolant may be immiscible with water at the temperature of the separating. In certain embodiments, for example, the liquid coolant may be immiscible with water at the temperature of the condensing. In certain embodiments, for example, the liquid coolant may be substantially water-free.

C. In certain embodiments, for example, the liquid coolant may absorb formaldehyde from the liquid product. In certain embodiments, for example, the method may further comprise: introducing an absorbent for formaldehyde into a vessel where the condensing occurs. In certain embodiments, for example, the absorbent may be bentonite.

Certain embodiments may provide, for example, a method for producing a low-formaldehyde liquid product having a ratio of no more than 150 ppm formaldehyde per 1° BX of the low-formaldehyde liquid product. In certain embodiments, for example, the method may comprise: pyrolyzing biomass in a biomass-containing stream to form a gaseous pyrolytic stream comprising water. In certain embodiments, for example, the method may comprise: introducing the gaseous pyrolytic stream into a separation unit. In certain embodiments, for example, the method may comprise: recirculating a substantially water-free liquid coolant stream from an outlet of the separation unit to an inlet of the separation unit. In certain embodiments, for example, the method may comprise: recovering substantially all of the water present in the gaseous pyrolytic stream from the separation unit in a first stream consisting of the liquid product and a second stream consisting of a non-condensed portion of the gaseous pyrolytic stream.

A. In certain embodiments, for example, condensed water in the separation unit may have a residence time in the separation unit of less than 2 hours, for example condensed water in the separation unit may have a residence time in the separation unit of less than 90 minutes, of less than 60 minutes, of less than 30 minutes, of less than 20 minutes, of less than 10 minutes, of less than 5 minutes, or condensed water in the separation unit may have a residence time in the separation unit of less than 1 minute. In certain embodiments, for example, condensed water in the separation unit may have a residence time in the separation unit of between 1 minute and 2 hours, condensed water in the separation unit may have a residence time in the separation unit of between 3 minutes and 1 hour, 3 minutes and 30 minutes, 1 minute and 20 minutes, 1 minute and 10 minutes, 1 minute and 5 minutes, 20 minutes and 90 minutes, or condensed water in the separation unit may have a residence time in the separation unit of between 10 minutes and 45 minutes.

B. In certain embodiments, for example, substantially all water present in the separation unit may comprise water present in the gaseous pyrolytic stream. In certain embodiments, for example, at least 70% of water present in the separation unit may comprise water introduced in the gaseous pyrolytic stream, for example at least 80%, at least 95%, or at least 99% of water present in the separation unit may comprise water introduced in the gaseous pyrolytic stream. In certain embodiments, for example, between 70% and 100% of water present in the separation unit may comprise water introduced in the gaseous pyrolytic stream, for example between 80% and 100%, between 90% and 100%, between 95% and 100%, or between 99% and 100% of water present in the separation unit may comprise water introduced in the gaseous pyrolytic stream.

C. In certain embodiments, for example, coolant comprising the liquid coolant stream may be immiscible with water.

D. In certain embodiments, for example, the separation unit may be a condenser. In certain embodiments, for example, the condenser may be a single stage condenser. In certain embodiments, for example, the condenser may be a single pass condenser. In certain embodiments, for example, the condenser may be a quench condenser.

E. In certain embodiments, for example, the liquid coolant stream may be recirculated at a ratio of liquid coolant to the biomass in the biomass-containing stream of at least 50:1 (v/v), for example the liquid coolant stream may be recirculated at a ratio of liquid coolant to the biomass in the biomass-containing stream of at least 75:1 (v/v), of at least 100:1 (v/v), of at least 115:1 (v/v), of at least 125:1 (v/v), of at least 140:1 (v/v), of at least 150:1 (v/v), of at least 175:1 (v/v), or the liquid coolant stream may be recirculated at a ratio of liquid coolant to the biomass in the biomass-containing stream of at least 200:1 (v/v). In certain embodiments, for example, the liquid coolant stream may be recirculated at a ratio of liquid coolant to the biomass in the biomass-containing stream of between 50:1 (v/v) and 200:1 (v/v), for example the liquid coolant stream may be recirculated at a ratio of liquid coolant to the biomass in the biomass-containing stream of between 50:1 (v/v) and 175:1 (v/v), of between 75:1 (v/v) and 175:1 (v/v), of between 100:1 (v/v) and 200:1 (v/v), of between 125:1 (v/v) and 175:1 (v/v), or the liquid coolant stream may be recirculated at a ratio of liquid coolant to the biomass in the biomass-containing stream of between 110:1 (v/v) and 125:1 (v/v).

In certain embodiments, for example, the liquid coolant stream may be recirculated at a ratio of liquid coolant to pyrolysis products in the gaseous pyrolytic stream of at least 50:1 (w/w), for example the liquid coolant stream may be recirculated at a ratio of liquid coolant to pyrolysis products in the gaseous pyrolytic stream of at least 75:1 (w/w), of at least 100:1 (w/w), of at least 115:1 (w/w), of at least 125:1 (w/w), of at least 140:1 (w/w), of at least 150:1 (w/w), of at least 175:1 (w/w), or the liquid coolant stream may be recirculated at a ratio of liquid coolant to pyrolysis products in the gaseous pyrolytic stream of at least 200:1 (w/w). In certain embodiments, for example, the liquid coolant stream may be recirculated at a ratio of liquid coolant to pyrolysis products in the gaseous pyrolytic stream of between 50:1 (w/w) and 200:1 (w/w), for example the liquid coolant stream may be recirculated at a ratio of liquid coolant to pyrolysis products in the gaseous pyrolytic stream of between 50:1 (w/w) and 175:1 (w/w), of between 75:1 (w/w) and 175:1 (w/w), of between 100:1 (w/w) and 200:1 (w/w), of between 125:1 (w/w) and 175:1 (w/w), or the liquid coolant stream may be recirculated at a ratio of liquid coolant to pyrolysis products in the gaseous pyrolytic stream of between 125:1 (w/w) and 150:1 (w/w).

In certain embodiments, for example, the liquid coolant stream may be recirculated at a ratio of liquid coolant to liquid product in the first stream of at least 50:1 (v/v), for example the liquid coolant stream may be recirculated at a ratio of liquid coolant to liquid product in the first stream of at least 75:1 (v/v), of at least 100:1 (v/v), of at least 115:1 (v/v), of at least 125:1 (v/v), of at least 140:1 (v/v), of at least 150:1 (v/v), of at least 175:1 (v/v), or the liquid coolant stream may be recirculated at a ratio of liquid coolant to liquid product in the first stream of at least 200:1 (v/v). In certain embodiments, for example, the liquid coolant stream may be recirculated at a ratio of liquid coolant to liquid product in the first stream of between 50:1 (v/v) and 200:1 (v/v), for example the liquid coolant stream may be recirculated at a ratio of liquid coolant to liquid product in the first stream of between 50:1 (v/v) and 175:1 (v/v), of between 75:1 (v/v) and 175:1 (v/v), of between 100:1 (v/v) and 200:1 (v/v), of between 125:1 (v/v) and 175:1 (v/v), or the liquid coolant stream may be recirculated at a ratio of liquid coolant to liquid product in the first stream of between 125:1 (v/v) and 150:1 (v/v).

In certain embodiments, for example, the ratio of liquid coolant to liquid product in the separation unit may be at least 5:1 (v/v), for example the ratio of liquid coolant to liquid product in the separation unit may be at least 7:1 (v/v), at least 10:1 (v/v), at least 15:1 (v/v), at least 20:1 (v/v), at least 25:1 (v/v), or the ratio of liquid coolant to liquid product in the separation unit may be at least 50:1 (v/v). In certain embodiments, for example, the ratio of liquid coolant to liquid product in the separation unit may be between 5:1 (v/v) and 50:1 (v/v), for example the ratio of liquid coolant to liquid product in the separation unit may be between 5:1 (v/v) and 25:1 (v/v), between 5:1 (v/v) and 15:1 (v/v), between 10:1 (v/v) and 25:1 (v/v), or the ratio of liquid coolant to liquid product in the separation unit may be between 5:1 (v/v) and 10:1 (v/v).

F. In certain embodiments, for example, the liquid coolant stream may be passed through a heat exchanger and cooled by a temperature of between 1° C. and 15° C., for example the liquid coolant stream may be passed through a heat exchanger and cooled by a temperature of between 1° C. and 10° C., of between 2° C. and 7° C., or the liquid coolant stream may be passed through a heat exchanger and cooled by a temperature of between 5° C. and 10° C.

Certain embodiments may provide, for example, a method for producing a low-formaldehyde product having a ratio of no more than 150 ppm formaldehyde per 1° BX of the low-formaldehyde product. In certain embodiments, for example, the method may comprise: introducing one or more biomass components to a thermal conversion reactor to form gaseous conversion products. In certain embodiments, for example, the method may comprise: passing the gaseous conversion products into a separation unit operating at a temperature of between 20° C. and 60° C. within 0.2 seconds of the introducing. In certain embodiments, for example, the method may comprise: obtaining the low-formaldehyde product, comprising: contacting the gaseous conversion products in the separation unit with a substantially water-free liquid coolant.

A. In certain embodiments, for example, the low-formaldehyde product may have a ratio of at least 0.01 wt. % hydroxyacetaldehyde per 1° BX of the low-formaldehyde product, for example, the low-formaldehyde product may have a ratio of at least 0.05 wt. % hydroxyacetaldehyde per 1° BX of the low-formaldehyde product, of at least 0.1 wt. % hydroxyacetaldehyde per 1° BX of the low-formaldehyde product, of at least 0.2 wt. % hydroxyacetaldehyde per 1° BX of the low-formaldehyde product, of at least 0.3 wt. % hydroxyacetaldehyde per 1° BX of the low-formaldehyde product, of at least 0.35 wt. % hydroxyacetaldehyde per 1° BX of the low-formaldehyde product, of at least 0.4 wt. % hydroxyacetaldehyde per 1° BX of the low-formaldehyde product, of at least 0.45 wt. % hydroxyacetaldehyde per 1° BX of the low-formaldehyde product, or the low-formaldehyde product may have a ratio of at least 0.5 wt. % hydroxyacetaldehyde per 1° BX of the low-formaldehyde product. In certain embodiments, for example, the low-formaldehyde product may have a ratio of between 0.05 wt. % hydroxyacetaldehyde per 1° BX of the low-formaldehyde product and 0.5 wt. % hydroxyacetaldehyde per 1° BX of the low-formaldehyde product, for example the low-formaldehyde product may have a ratio of between 0.1 wt. % hydroxyacetaldehyde per 1° BX of the low-formaldehyde product and 0.5 wt. % hydroxyacetaldehyde per 1° BX of the low-formaldehyde product, of between 0.2 wt. % hydroxyacetaldehyde per 1° BX of the low-formaldehyde product and 0.5 wt. % hydroxyacetaldehyde per 1° BX of the low-formaldehyde product, of between 0.3 wt. % hydroxyacetaldehyde per 1° BX of the low-formaldehyde product and 0.5 wt. % hydroxyacetaldehyde per 1° BX of the low-formaldehyde product, or the low-formaldehyde product may have a ratio of between 0.4 wt. % hydroxyacetaldehyde per 1° BX of the low-formaldehyde product and 0.5 wt. % hydroxyacetaldehyde per 1° BX of the low-formaldehyde product.

B. In certain embodiments, for example, the temperature may be less than 59° C., for example the temperature may be less than 59° C., less than 58° C., less than 57° C., less than 56° C., less than 55° C., less than 54° C., less than 53° C., less than 52° C., less than 51° C., less than 50° C., less than 49° C., less than 48° C., less than 47° C., less than 46° C., less than 45° C., less than 44° C., less than 43° C., less than 42° C., less than 41° C., less than 40° C., less than 39° C., less than 38° C., less than 37° C., less than 36° C., less than 35° C., less than 34° C., less than 33° C., less than 32° C., less than 31° C., less than 30° C., less than 29° C., less than 28° C., less than 27° C., less than 26° C., less than 25° C., less than 24° C., less than 23° C., less than 22° C., or the temperature may be less than less than 21° C.

In certain embodiments, for example, the passing may be within 4 seconds of the introducing, for example the passing may be within 3 seconds of the introducing, for example within 2 seconds of the introducing, within 1 second of the introducing, or the passing may be within 0.5 seconds of the introducing. In certain embodiments, for example, the passing may be between 0.5 seconds and 5 seconds of the introducing, for example the passing may be between 1 second and 4 seconds of the introducing, between 1 second and 3 seconds of the passing, or the passing may be between 2 seconds and 4 seconds of the introducing.

In certain embodiments, for example, the gaseous conversion products may enter the separation unit at a temperature that is within 50° C. (for example within 50° C., within 25° C., within 10° C., or within 5° C.) of a temperature at which the gaseous conversion products leave the thermal conversion reactor. In certain embodiments, for example, the gaseous conversion products may enter the separation unit at a temperature of at least 400° C., for example, the gaseous conversion products may enter the separation unit at a temperature of at least 425° C., of at least 450° C., of at least 475° C., or the gaseous conversion products may enter the separation unit at a temperature of at least 500° C.

In certain embodiments, for example, the gaseous conversion products may be cooled within 1 second of entering the separation unit to a temperature of less than 100° C., for example, the gaseous conversion products may be cooled within 0.5 seconds of entering the separation unit to a temperature of less than 75° C., cooled with 0.2 seconds of entering the separation unit to a temperature of less than 55° C., cooled within 0.1 seconds of entering the separation unit to a temperature of less than 55° C., cooled within 0.1 seconds of entering the separation unit to a temperature of less than 50° C., cooled within 0.02 seconds of entering the separation unit to a temperature of less than 55° C., or the gaseous conversion products may be cooled within 0.02 seconds of entering the separation unit to a temperature of less than 50° C.

C. In certain embodiments, for example, the separation unit may be a single stage condenser. In certain embodiments, for example, the condenser may be a vertically oriented cylindrical vessel characterized by an average diameter of one or more cylindrical portions of the vessel.

D. In certain embodiments, for example, a solubility of water in the liquid coolant at 25° C. may be less than 10000 ppm, for example a solubility of water in the liquid coolant at 25° C. may be less than 1000 ppm, less than 750 ppm, less than 500 ppm, less than 250 ppm, less than 100 ppm, less than 50 ppm, less than 25 ppm, less than 10 ppm, or a solubility of water in the liquid coolant at 25° C. may be less than 1 ppm. In certain embodiments, for example, a solubility of water in the liquid coolant at 25° C. may be between 1 ppm and 10000 ppm, for example a solubility of water in the liquid coolant at 25° C. may be between 1 ppm and 10 ppm, between 10 ppm and 100 ppm, between 100 ppm and 1000 ppm, or a solubility of water in the liquid coolant at 25° C. may be between 1000 ppm and 10000 ppm.

In certain embodiments, for example, a solubility of the liquid coolant in water at 25° C. may be less than 10000 ppm, for example a solubility of the liquid coolant in water at 25° C. may be less than 1000 ppm, less than 750 ppm, less than 500 ppm, less than 250 ppm, less than 100 ppm, less than 50 ppm, less than 25 ppm, less than 10 ppm, or a solubility of the liquid coolant in water at 25° C. may be less than 1 ppm. In certain embodiments, for example, a solubility of the liquid coolant in water at 25° C. may be between 1 ppm and 10000 ppm, for example a solubility of the liquid coolant in water at 25° C. may be between 1 ppm and 10 ppm, between 10 ppm and 100 ppm, between 100 ppm and 1000 ppm, or a solubility of the liquid coolant in water at 25° C. may be between 1000 ppm and 10000 ppm water.

In certain embodiments, for example, the liquid coolant may absorb less than 5% of water present in the gaseous conversion products, for example the liquid coolant may absorb less than 2.5% of water present in the gaseous conversion products, less than 1% of water present in the gaseous conversion products, less than 0.5% of water present in the gaseous conversion products, or the liquid coolant may absorb less than 0.05% of water present in the gaseous conversion products.

In certain embodiments, for example, the liquid coolant may have a heat capacity of between 0.5 kJ/kg-° C. and 5 kJ/kg-° C., for example the liquid coolant may have a heat capacity of between 1 kJ/kg-° C. and 5 kJ/kg-° C., of between 1.5 kJ/kg-° C. and 4 kJ/kg-° C., of between 2 kJ/kg-° C. and 4 kJ/kg-° C., of between 1 kJ/kg-° C. and 3 kJ/kg-° C., or the liquid coolant may have a heat capacity of between 2 kJ/kg-° C. and 4 kJ/kg-° C.

E. In certain embodiments, for example, the liquid coolant may be recirculated from an outlet of the separation unit to an inlet of the separation unit. In certain embodiments, for example, the liquid coolant may be recirculated at a ratio of liquid coolant to low-formaldehyde product of at least 50:1 (v/v), for example the liquid coolant may be recirculated at a ratio of liquid coolant to low-formaldehyde product of at least 75:1 (v/v), of at least 100:1 (v/v), of at least 115:1 (v/v), of at least 125:1 (v/v), of at least 140:1 (v/v), of at least 150:1 (v/v), of at least 175:1 (v/v), or the liquid coolant may be recirculated at a ratio of liquid coolant to low-formaldehyde product of at least 200:1 (v/v). In certain embodiments, for example, the liquid coolant may be recirculated at a ratio of liquid coolant to low-formaldehyde product of between 50:1 (v/v) and 200:1 (v/v), for example the liquid coolant may be recirculated at a ratio of liquid coolant to low-formaldehyde product of between 50:1 (v/v) and 175:1 (v/v), of between 75:1 (v/v) and 175:1 (v/v), of between 100:1 (v/v) and 200:1 (v/v), of between 125:1 (v/v) and 175:1 (v/v), or the liquid coolant may be recirculated at a ratio of liquid coolant to low-formaldehyde product of between 125:1 (v/v) and 150:1 (v/v). In certain embodiments, for example, the liquid coolant may be recirculated at a recycle ratio of liquid coolant to low-formaldehyde product of at least 5:1 (v/v) per square foot average diameter of the separation unit, for example the liquid coolant may be recirculated at a recycle ratio of liquid coolant to low-formaldehyde product of at least 10:1 (v/v) per square foot average diameter of the separation unit, at least 15:1 (v/v) per square foot average diameter of the separation unit, or the liquid coolant may be recirculated at a recycle ratio of liquid coolant to low-formaldehyde product of at least 20:1 (v/v) per square foot average diameter of the separation unit. In certain embodiments, for example, the liquid coolant may be recirculated at a recycle ratio of liquid coolant to low-formaldehyde product of between 5:1 (v/v) and 20:1 (v/v) per square foot average diameter of the separation unit, for example the liquid coolant may be recirculated at a recycle ratio of liquid coolant to low-formaldehyde product of between 10:1 (v/v) and 20:1 (v/v) per square foot average diameter of the separation unit, or the liquid coolant may be recirculated at a recycle ratio of liquid coolant to low-formaldehyde product of between 10:1 (v/v) and 15:1 (v/v) per square foot average diameter of the separation unit. In certain embodiments, for example, the gaseous conversion products are contacted with downward flow of recirculated liquid coolant at a ratio of recirculated liquid coolant to low-formaldehyde product of at least 5:1 (v/v) per square foot average diameter of the separation unit, for example the vapor conversion products are contacted with downward flow of recirculated liquid coolant at a ratio of recirculated liquid coolant to low-formaldehyde product of at least 10:1 (v/v) per square foot average diameter of the separation unit, at least 15:1 (v/v) per square foot average diameter of the separation unit, or the gaseous conversion products are contacted with downward flow of recirculated liquid coolant at a ratio of recirculated liquid coolant to low-formaldehyde product of at least 20:1 (v/v) per square foot average diameter of the separation unit. In certain embodiments, for example, the gaseous conversion products are contacted with downward flow of recirculated liquid coolant at a ratio of recirculated liquid coolant to low-formaldehyde product of between 5:1 (v/v) and 20:1 (v/v) per square foot average diameter of the separation unit, for example the gaseous conversion products are contacted with downward flow of recirculated liquid coolant at a ratio of recirculated liquid coolant to low-formaldehyde product of between 10:1 (v/v) and 20:1 (v/v) per square foot average diameter of the separation unit, or the gaseous conversion products are contacted with downward flow of recirculated liquid coolant at a ratio of recirculated liquid coolant to low-formaldehyde product of between 10:1 (v/v) and 15:1 (v/v) per square foot average diameter of the separation unit. In certain embodiments, for example, the downward flow of recirculated liquid coolant may consist of a spray of liquid coolant generated by one or more liquid distributors (for example one of the liquid distributors disclosed in the INCORPORATED REFERENCES). In certain embodiments, for example, the one or more distributors may comprise nozzle orifices having a diameter of between 0.1 and 6 mm, for example the one or more distributors may comprise nozzle orifices having a diameter of between 1 and 5 mm, of between 1 and 4 mm, of between 2 and 5 mm, or the one or more distributors may comprise nozzle orifices having a diameter of between 2 and 4 mm. In certain embodiments, for example, the spray may consist of droplets having an average size of between 0.1 and 6 mm when the spray exits the one or more liquid distributors, for example the spray may consist of droplets having an average size of between 1 and 5 mm when the spray exits the one or more liquid distributors, of between 1 and 4 mm when the spray exits the one or more liquid distributors, of between 2 and 5 mm when the spray exits the one or more liquid distributors, or the spray may consist of droplets having an average size of between 2 and 4 mm when the spray exits the one or more liquid distributors.

In certain embodiments, for example, the ratio of low-formaldehyde product to liquid coolant in the separation unit may be at least 5:1 (v/v), for example the ratio of low-formaldehyde product to liquid coolant in the separation unit may be at least 7:1 (v/v), at least 10:1 (v/v), at least 15:1 (v/v), at least 20:1 (v/v), at least 25:1 (v/v), or the ratio of ratio of low-formaldehyde product to liquid coolant in the separation unit may be at least 50:1 (v/v). In certain embodiments, for example, the ratio of ratio of low-formaldehyde product to liquid coolant in the separation unit may be between 5:1 (v/v) and 50:1 (v/v), for example the ratio of ratio of low-formaldehyde product to liquid coolant in the separation unit may be between 5:1 (v/v) and 25:1 (v/v), between 5:1 (v/v) and 15:1 (v/v), between 10:1 (v/v) and 25:1 (v/v), or the ratio of ratio of low-formaldehyde product to liquid coolant in the separation unit may be between 5:1 (v/v) and 10:1 (v/v).

Certain embodiments may provide, for example, a method for converting at least 50 wt. % of one or more biomass components into a pyrolytic liquid product that comprises at least 25 wt. % hydroxyacetaldehyde and less than 5000 ppm formaldehyde. In certain embodiments, for example, the method may comprise: introducing the one or more biomass components to a pyrolysis reactor operating at a temperature of between 400° C. and 600° C. to form pyrolytic gases. In certain embodiments, for example, the method may comprise: selecting a water-free liquid coolant that is at least partially immiscible with the pyrolytic liquid product. In certain embodiments, for example, the method may comprise: contacting the pyrolytic gases with the liquid coolant in a single stage condenser operating at a temperature of between 20° C. and 60° C. and a residence time of less than 10 minutes. In certain embodiments, for example, the method may comprise: recovering the pyrolytic liquid product.

A. In certain embodiments, for example, the method may further comprise: further recovering at least a portion of the liquid coolant from the single stage condenser in different liquid phases.

B. In certain embodiments, for example, the gaseous conversion products may cooled to a temperature of between 20° C. and 60° C. in the single stage condenser.

In certain embodiments, for example, the gaseous conversion products may be cooled to the temperature of between 20° C. and 60° C. within 0.2 seconds of the introducing.

Certain embodiments may provide, for example, a method of forming a pyrolytic liquid product, comprising: i) introducing a predominately simple sugar biomass to a pyrolysis reactor operating at a temperature above 400° C. to form pyrolytic gases; ii) condensing at least a portion of the pyrolytic gases with a non-aqueous liquid in a concurrent flow condenser operating at a temperature between 10° C. and 50° C. with a residence time of less than 10 minutes; and iii) separating the condensed pyrolytic gases from the non-aqueous liquid to recover a pyrolytic liquid product.

Certain embodiments may provide, for example, a method of forming a hydroxyacetaldehyde-rich liquid, comprising: i) introducing a predominately simple sugar biomass to a pyrolysis reactor operating at a temperature above 400° C. to form pyrolytic gases; ii) condensing at least a portion of the pyrolytic gases with a non-aqueous liquid in a concurrent flow condenser operating at a temperature between 20° C. and 50° C. with a residence time of less than 10 minutes; and iii) separating the condensed pyrolytic gases from the non-aqueous liquid to recover the rich liquid having a ratio formaldehyde to hydroxyacetaldehyde of less than 0.02.

Certain embodiments may provide, for example, a method for producing a low-formaldehyde pyrolytic liquid having a ratio of formaldehyde-to-hydroxyacetaldehyde of no more than 0.02 (w/w), comprising: i) pyrolyzing dextrose at a temperature of between 400° C. and 500° C. to form gaseous pyrolysis products; ii) condensing at least 50 wt. % of the gaseous pyrolysis products to form the low-formaldehyde product in a single stage quench condenser, comprising: contacting the gaseous pyrolysis products with dodecane; and iii) separating at least a portion of the low-formaldehyde pyrolytic liquid from the dodecane.

Certain embodiments may provide, for example, a method for producing a liquid product having a ratio of no more than 100 ppm formaldehyde per 1° BX of the liquid product and a ratio of at least 0.45 hydroxyacetaldehyde per 1° BX of the liquid product, comprising: i) introducing a biomass-containing stream to a fast pyrolysis reactor to form a water-containing gaseous pyrolytic stream at a reaction temperature of between 350° C. at 500° C.; ii) passing the gaseous pyrolytic stream, at a temperature that is within 20° C. of the reaction temperature, into a single stage quench condenser within 2 seconds of the introducing; iii) forming the liquid product by cooling the gaseous conversion products in the single stage quench condenser to a temperature of between 10° C. and 50° C. within 0.2 seconds of the passing; iv) recirculating a substantially water-free liquid coolant stream from an outlet of the single stage quench condenser to an inlet of the single stage quench condenser at a ratio of the liquid coolant stream to the gaseous pyrolytic stream of at least 100:1 (w/w); and v) recovering substantially all of the water present in the gaseous pyrolytic stream from the single stage quench condenser in a first stream consisting of the liquid product and a second stream consisting of a non-condensed portion of the gaseous pyrolytic stream.

Certain embodiments may provide, for example, a method for producing a liquid product having a ratio of no more than 100 ppm formaldehyde per 1° BX of the liquid product and a ratio of at least 0.45 hydroxyacetaldehyde per 1° BX of the liquid product, comprising: i) introducing an aqueous glucose stream at a concentration of at least 50° BX to a fast pyrolysis reactor to form a water-containing gaseous pyrolytic stream at a reaction temperature of between 350° C. at 500° C.; ii) passing the gaseous pyrolytic stream, at a temperature that is within 20° C. of the reaction temperature, into a single stage quench condenser within 2 seconds of the introducing; iii) forming the liquid product by cooling the gaseous conversion products in the single stage quench condenser to a temperature of between 10° C. and 50° C. within 0.2 seconds of the passing; iv) recirculating a substantially water-free dodecane stream from an outlet of the single stage quench condenser to an inlet of the single stage quench condenser at a ratio of the dodecane stream to the aqueous glucose stream of at least 50:1 (v/v); and v) recovering substantially all of the water present in the gaseous pyrolytic stream from the single stage quench condenser in a first stream consisting of the liquid product and a second stream consisting of a non-condensed portion of the gaseous pyrolytic stream.

Certain embodiments may provide, for example, a method for producing a liquid product having a ratio of no more than 40 ppm formaldehyde per 1° BX of the liquid product and a ratio of at least 0.45 hydroxyacetaldehyde per 1° BX of the liquid product, comprising: i) introducing particulate sugar to a fast pyrolysis reactor to form a water-containing gaseous pyrolytic stream at a reaction temperature of between 350° C. at 500° C.; ii) passing the gaseous pyrolytic stream, at a temperature that is within 20° C. of the reaction temperature, into a single stage quench condenser within 2 seconds of the introducing; iii) forming the liquid product by cooling the gaseous conversion products in the single stage quench condenser to a temperature of between 10° C. and 50° C. within 0.2 seconds of the passing; iv) recirculating a substantially water-free dodecane stream from an outlet of the single stage quench condenser to an inlet of the single stage quench condenser at a ratio of the dodecane stream to the particulate sugar of at least 50:1 (w/w); and v) recovering substantially all of the water present in the gaseous pyrolytic stream from the single stage quench condenser in a first stream consisting of the liquid product and a second stream consisting of a non-condensed portion of the gaseous pyrolytic stream.

Certain embodiments may provide, for example, a method for producing a low-formaldehyde product having a ratio of no more than 150 ppm formaldehyde per 1° BX of the low-formaldehyde product, comprising: i) pyrolyzing biomass to form gaseous pyrolysis products; ii) condensing a portion of the gaseous pyrolysis products to form the low-formaldehyde product, comprising: contacting the gaseous pyrolysis products with a nonaqueous coolant; and iii) separating at least a portion of the low-formaldehyde product from the nonaqueous coolant.

Certain embodiments may provide, for example, a method for producing a low-formaldehyde product having a ratio of formaldehyde-to-hydroxyacetaldehyde of no more than 0.02 (w/w), comprising: i) pyrolyzing one or more simple sugars to form gaseous pyrolysis products; ii) condensing a portion of the gaseous pyrolysis products to form the low-formaldehyde product, comprising: contacting the gaseous pyrolysis products with a nonaqueous coolant; and iii) separating at least a portion of the low-formaldehyde product from the nonaqueous coolant.

Certain embodiments may provide, for example, a method for producing a low-formaldehyde product having a ratio of formaldehyde-to-hydroxyacetaldehyde of no more than 0.02 (w/w), comprising: i) pyrolyzing one or more simple sugars to form gaseous pyrolysis products; ii) condensing a portion of the gaseous pyrolysis products to form the low-formaldehyde product, comprising: contacting the gaseous pyrolysis products with a liquid coolant having a formaldehyde solubility at 25° C. of less than 100 ppm formaldehyde in the liquid coolant; and iii) separating at least a portion of the low-formaldehyde product from the liquid coolant.

Certain embodiments may provide, for example, a method for producing a low-formaldehyde product having a ratio of formaldehyde-to-hydroxyacetaldehyde of no more than 0.02 (w/w), comprising: i) pyrolyzing one or more simple sugars to form gaseous pyrolysis products; ii) condensing a portion of the gaseous pyrolysis products to form the low-formaldehyde product, comprising: contacting the gaseous pyrolysis products with a liquid coolant having a water solubility at 25° C. of less than 100 ppm water in the liquid coolant; and iii) separating at least a portion of the low-formaldehyde product from the liquid coolant.

Certain embodiments may provide, for example, a method for producing a low-formaldehyde liquid product having a ratio of no more than 150 ppm formaldehyde per 1° BX of the low-formaldehyde liquid product, comprising: i) pyrolyzing one or more biomass components to form gaseous pyrolysis products; ii) introducing the gaseous pyrolysis products into a separation unit; iii) recirculated a liquid coolant having a water solubility at 25° C. of less than 100 ppm water from an outlet of the separation unit to an inlet of the separation unit; and iv) recovering the liquid product comprising at least 50 wt. % of the gaseous pyrolysis products from the separation unit.

Certain embodiments may provide, for example, a method for producing a low-formaldehyde liquid product having a ratio of no more than 150 ppm formaldehyde per 1° BX of the low-formaldehyde liquid product, comprising: i) pyrolyzing one or more biomass components to form gaseous pyrolysis products; ii) condensing a portion of the gaseous pyrolysis products to form the low-formaldehyde product, comprising contacting the gaseous pyrolysis products with a liquid coolant that is immiscible with the liquid product; and iii) physically separating the liquid product from the liquid coolant.

Certain embodiments may provide, for example, a method for producing a low-formaldehyde liquid product having a ratio of no more than 150 ppm formaldehyde per 1° BX of the low-formaldehyde liquid product, comprising: i) pyrolyzing biomass in a biomass-containing stream to form a gaseous pyrolytic stream comprising water; ii) introducing the gaseous pyrolytic stream into a separation unit; iii) recirculating a substantially water-free liquid coolant stream from an outlet of the separation unit to an inlet of the separation unit; and iv) recovering substantially all of the water present in the gaseous pyrolytic stream from the separation unit in a first stream consisting of the liquid product and a second stream consisting of a non-condensed portion of the gaseous pyrolytic stream.

Certain embodiments may provide, for example, a method for producing a low-formaldehyde product having a ratio of no more than 150 ppm formaldehyde per 1° BX of the low-formaldehyde product, comprising: i) introducing one or more biomass components to a thermal conversion reactor to form gaseous conversion products; ii) passing the gaseous conversion products into a separation unit operating at a temperature of between 20° C. and 60° C. within 0.2 seconds of the introducing; and iii) obtaining the low-formaldehyde product, comprising: contacting the gaseous conversion products in the separation unit with a substantially water-free liquid coolant.

Certain embodiments may provide, for example, a method for converting at least 50 wt. % of one or more biomass components into a pyrolytic liquid product that comprises at least 25 wt. % hydroxyacetaldehyde and less than 5000 ppm formaldehyde, comprising: i) introducing the one or more biomass components to a pyrolysis reactor operating at a temperature of between 400° C. and 600° C. to form pyrolytic gases; ii) selecting a water-free liquid coolant that is at least partially immiscible with the pyrolytic liquid product; iii) contacting the pyrolytic gases with the liquid coolant in a single stage condenser operating at a temperature of between 20° C. and 60° C. and a residence time of less than 10 minutes; and iv) recovering the pyrolytic liquid product.

DETAILED DESCRIPTION OF THE DRAWINGS

DETAILED DESCRIPTION OF THE INVENTION

The present disclosure is based, generally and in combination with other aspects disclosed herein, on the discovery that water present during quenching and condensation of thermally generated (for example pyrolytic) gases plays a significant role in determining the formaldehyde content of pyrolytic condensates. Providing a low water condensing environment, for example, can significantly reduce formaldehyde concentration in pyrolytic condensates, both in absolute terms and relative to desired chemical constituents. The present disclosure is further specifically based, in part, on the discovery that significant formaldehyde reduction can be achieved by employing a nonaqueous quench liquid in a primary quench condenser. Moreover, it has been discovered that elimination of water carrier from pyrolysis feedstocks can reduce formaldehyde concentration in condensed product condensates.

Figure 1:
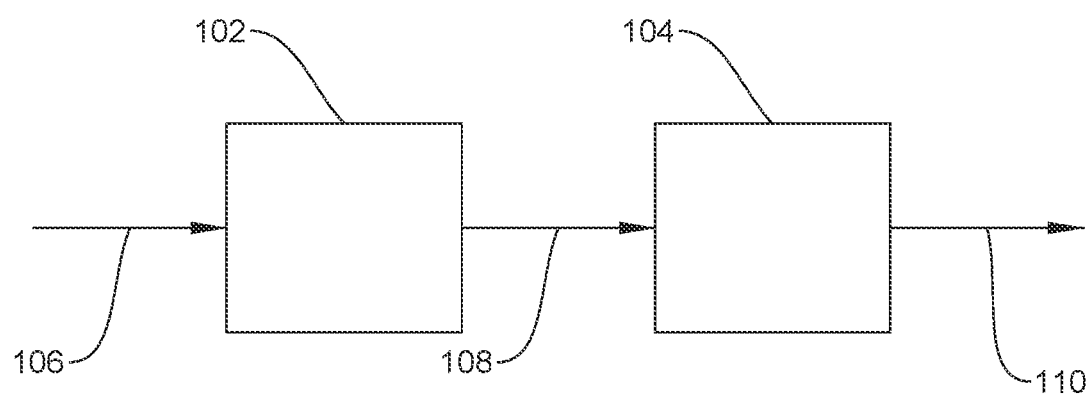
FIG. 1 is a schematic depiction of a thermal process comprising a nonaqueous quench condenser.

A schematic depiction of thermal process (for example one of the thermal processes disclosed in the INCORPORATED REFERENCES such as fast pyrolysis) embodiment 100 comprising a thermal reactor 102 and a quench condenser 104 is shown in FIG. 1. A biomass 106 is converted in the thermal reactor 102 to a thermal product gas 108 which is introduced to the quench condenser 104 and at least partially condensed to form a liquid product 110. The quench condenser 104 uses a nonaqueous quench medium to cool the thermal product gas 108 to form the liquid product 110.

The thermal reactor 102 can be any type of low oxygen thermal reactor effective to at least partially pyrolyze the biomass. The thermal reactor 102 can be any of the thermal reactors disclosed in the INCORPORATED REFER- ENCES. The thermal reactor 102 can be an upflow reactor using heat carrier particles in an entrained lift gas to mix with the biomass. The thermal reactor 102 can be a fluidized bed reactor. The thermal reactor 102 can be a rotating cone reactor. The thermal reactor 102 can be an ablative reactor. The thermal reactor 102 can be a screw or auger reactor.

The quench condenser 104 can comprise a single vessel. The quench condenser 104 can be any of the quench condensers disclosed in the INCORPORATED REFERENCES. The quench condenser 104 can comprise a multi-tray distillation column. The quench condenser 104 may comprise a recirculation loop to recirculate the quench medium from a lower portion of the quench condenser 104 to an upper portion of the quench condenser 104. The recirculation loop can include a heat exchanger to cool the quench medium. The quench condenser 104 can include a settling zone in a lower portion of the quench condenser 104 to provide phase separation between the quench medium and the liquid product. The quench condenser 104 may be in communication with a settling vessel to provide phase separation between the quench medium and the liquid product, and the quench medium returned to the quench condenser 104.

The nonaqueous quench medium can be selected from the nonexclusive group consisting of a petroleum-based liquid, liquid hydrocarbon, an unsaturated liquid hydrocarbon, a saturated liquid hydrocarbon, a hexane, a heptane, dodecane, a vegetable oil, diesel, a polysorbate, a polymer, a silicone oil, or a combination of two or more of the foregoing. The nonaqueous quench medium can be one or more of the quench media disclosed in the INCORPORATED REFERENCES.

The biomass 106 can be introduced to the thermal reactor 102 as a particulate solid. The biomass 106 can be introduced to the thermal reactor 102 as a suspension in a liquid, such as a suspension in water or a suspension in a nonaqueous coolant medium. The biomass 106 can be introduced to the thermal reactor 102 dissolved in an aqueous solution. The biomass 106 can be one or more of the biomasses disclosed herein and/or in the INCORPORATED REFERENCES. The biomass 106 can be a biomass selected from the non-exclusive group consisting of: a carbohydrate-containing biomass, a sugar-containing biomass (for example potatoes, sugar beets, milk such as cow's milk, or corn syrup), a starch (for example corn starch, potato starch, wheat starch, oat starch, tapioca starch, or rice starch), a monosaccharide, a disaccharide, a trisaccharide, a polysaccharide, glucose, glyceraldehyde, threose, erythrose, ribose, arabinose, xylose, lyxose, allose, altrose, mannose, gulose, idose, galactose, talose, sorbose, cellobiose, a glucose-containing polysaccharide, dextrose, invert sugar, lactose, malt syrup, molasses, starch hydrolysates and fractions thereof, fructose, maltose, sucrose, a cellobiose-containing biomass, a hemi-cellulose-containing biomass, a cellulose-containing biomass, wood, hardwood, softwood, bark, agricultural residues, silvicultural residues, seed, nuts, leaves, fruit fiber, plant-derived syrup, plant-derived extract, algae, grasses, forestry residues, municipal solid waste, construction and/or demolition debris, lignin-containing biomasswood residues, sawdust, slash bark, thinnings, forest cullings, begasse, corn fiber, corn stover, empty fruit bunches (EFB), fronds, palm fronds, flax, straw, low-ash straw, energy crops, palm oil, non-food-based biomass materials, crop residue, slash, pre-commercial thinnings and tree residue, annual covercrops, switchgrass, *miscanthus*, cellulosic containing components, cellulosic components of separated yard waste, cellulosic components of separated food waste, cellulosic components of separated municipal solid waste (MSW), holocellulose-containing biomass, for example, grasses, straw, paper, pulp, pulp residues, whitewood, partially de-lignified wood, other biomass carbonaceous feedstocks, or a combination of two or more of the foregoing.

The thermal product gas 108 can comprise a mixture of thermal degradation products of the biomass (for example any of the thermal degradation products disclosed in the INCORPORATED REFERENCES). The thermal product gas 108 can comprise hydrogen. The thermal product gas 108 can comprise methane. The thermal product gas 108 can comprise water. The thermal product gas 108 can comprise oxygen-containing hydrocarbons. The thermal product gas 108 can comprise one or more alcohols. The thermal product gas 108 can comprise one or more organic acids. The thermal product gas 108 can comprise one or more aldehydes. The thermal product gas 108 can comprise formaldehyde. The thermal product gas 108 can comprise hydroxyacetaldehyde (also referred to as glycolaldehyde). The thermal product gas 108 can comprise one or more carbonyl-containing compounds. The thermal product gas 108 can comprise formaldehyde. The thermal product gas 108 can comprise acetic acid. The thermal product gas 108 can comprise acetol. The thermal product gas 108 can comprise cyclotene. The thermal product gas 108 can comprise one or more of: 2-methoxyphenol; 2-methoxy-4-methylphenol; 4-ethyl-2-methoxyphenol; 1,4-dimethoxy-2-methylphenol; 2-methoxy-5-(or 4,6)(1-propenyl) phenol; 2,6-(or 3,4-)dimethoxyphenol; 2-methoxy-5-(or 4, or 6)(1-propenyl) phenol; 4-hydroxy-3-methoxybenzoic acid or 2,5-dimethoxybenzyl alcohol; (1,1-dimethylethyl)-1,2-benzenediol or 1-(4-hydroxy-3-methoxyphenyl)ethanone; 3,4-dimethoxybenzoic acid; 2,6-dimethoxy-4-(2-propenyl)-phenol; and 3,4' (or 3,3' or 4,4')-1,1'-biphenyl. The thermal product gas 108 can comprise an inert gas (for example an inert lift gas used in the thermal reactor).

The liquid product 110 can comprise a mixture of thermal degradation products of the biomass. The liquid product 110 can comprise water. The liquid product 110 can comprise oxygen-containing hydrocarbons. The liquid product 110 can comprise one or more alcohols. The liquid product 110 can comprise one or more organic acids. The liquid product 110 can comprise one or more aldehydes. The liquid product 110 can comprise formaldehyde. The liquid product 110 can comprise hydroxyacetaldehyde. The liquid product 110 can comprise one or more carbonyl-containing compounds. The liquid product 110 can comprise formaldehyde. The liquid product 110 can comprise acetic acid. The liquid product 110 can comprise acetol. The liquid product 110 can comprise cyclotene. The liquid product 110 can comprise one or more of: 2-methoxyphenol; 2-methoxy-4-methylphenol; 4-ethyl-2-methoxyphenol; 1,4-dimethoxy-2-methylphenol; 2-methoxy-5-(or 4,6)(1-propenyl) phenol; 2,6-(or 3,4-)dimethoxyphenol; 2-methoxy-5-(or 4, or 6)(1-propenyl) phenol; 4-hydroxy-3-methoxybenzoic acid or 2,5-dimethoxybenzyl alcohol; (1,1-dimethylethyl)-1,2-benzenediol or 1-(4-hydroxy-3-methoxyphenyl)ethanone; 3,4-dimethoxybenzoic acid; 2,6-dimethoxy-4-(2-propenyl)-phenol; and 3,4' (or 3,3' or 4,4')-1,1'-biphenyl. The liquid product 110 can comprise an inert gas (for example an inert lift gas used in the thermal reactor).

Figure 2:
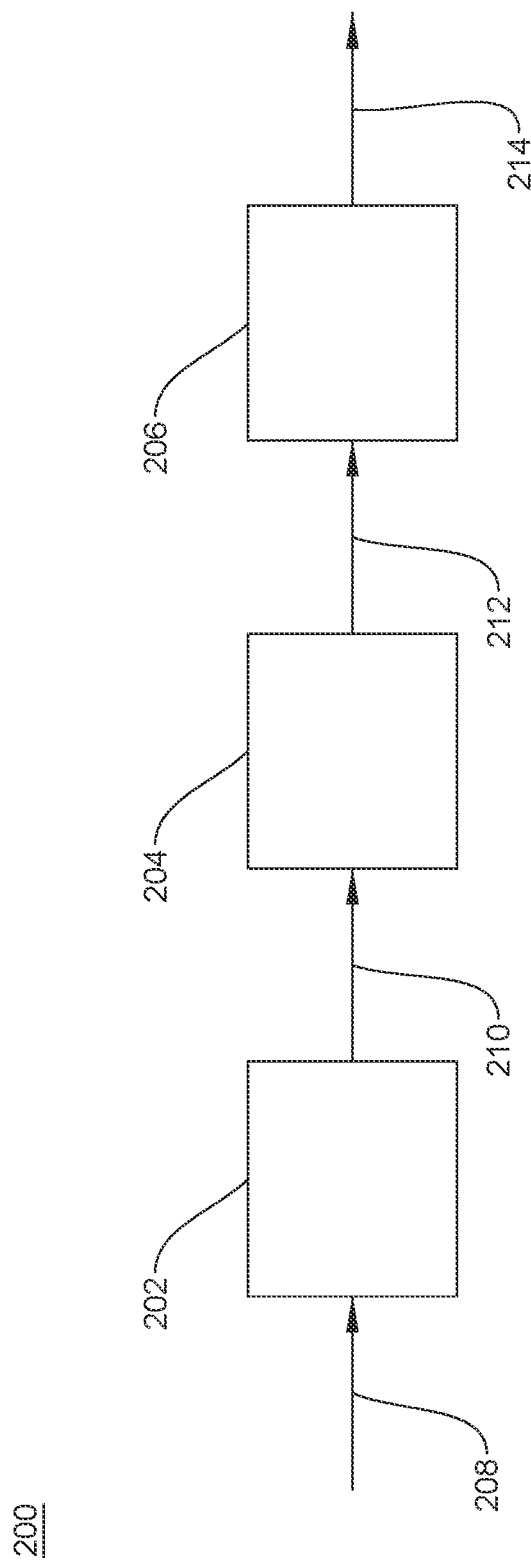
FIG. 2 is a schematic depiction of a thermal process comprising a formaldehyde removal component.

A schematic depiction of a thermal process embodiment 200 comprising a thermal reactor 202, one or more liquid recovery components 204, and a formaldehyde removal component 206 is shown in FIG. 2. A biomass 208 is converted in the thermal reactor 202 to a thermal product gas 210 which is introduced to the one or more liquid recovery components 204 and at least partially condensed to form a formaldehyde-containing condensate 212. The formaldehyde-containing condensate 212 is passed through the formaldehyde removal component 206 to form a liquid product 214. The liquid product 214 has a lower concentration of formaldehyde than the formaldehyde-containing condensate 212. The thermal reactor 202 may be any of the thermal reactors disclosed herein or in the INCORPORATED REFERENCES. The one or more liquid recovery components 204 may comprise one or more of the quench condensers disclosed herein. The one or more liquid recovery components 204 may comprise a chiller. The one or more liquid recovery components 204 may comprise a fiber bed filter. The one or more liquid recovery components 204 may comprise a demister. The formaldehyde removal component 206 can comprise an evaporator. The evaporator can operate under reduced pressure (for example under a vacuum). The formaldehyde removal component 206 can comprise a bentonite addition and filtration tank. The biomass 208 can be one or more of the biomasses disclosed herein and/or in the INCORPORATED REFERENCES. The thermal product gas 210 can comprise one or more of the thermal product gas components disclosed herein and/or in the INCORPORATED REFERENCES. The formaldehyde-containing condensate 212 and/or the liquid product 214 can comprise one or more of the liquid product components disclosed herein and/or in the INCORPORATED REFERENCES.

Figure 3:
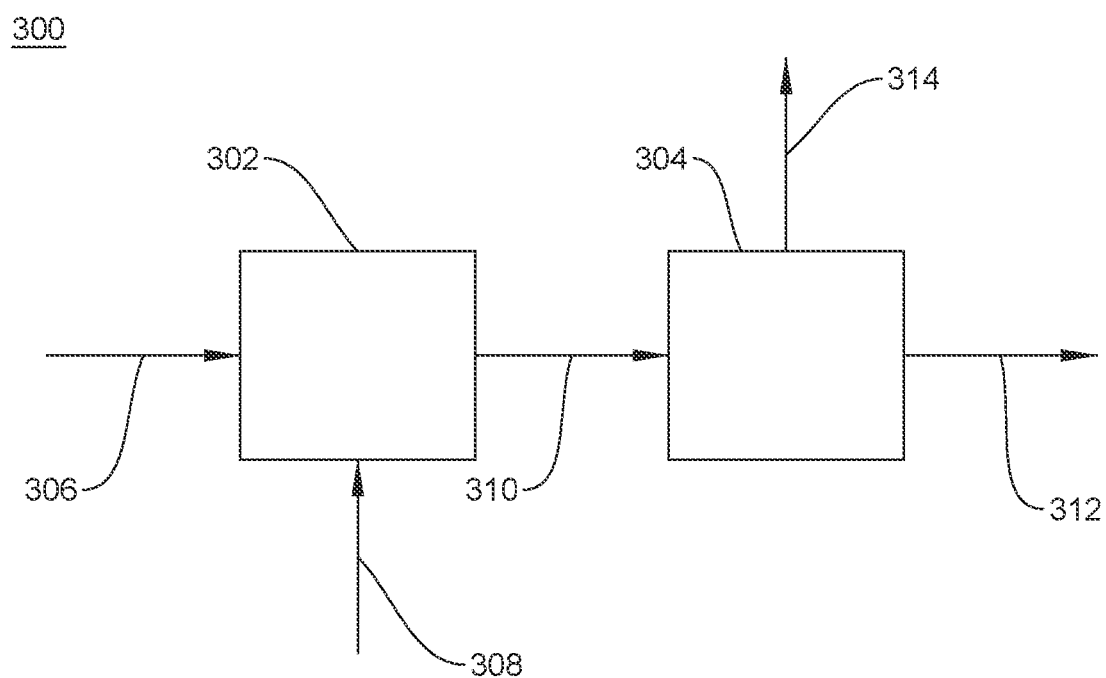
FIG. 3 is a schematic depiction of an upflow thermal process using a formaldehyde-free lift gas.

A schematic depiction of a thermal process embodiment 300 comprising an upflow fast pyrolysis reactor 302 and one or more liquid recovery components 304 is shown in FIG. 3. A biomass 306 and formaldehyde-free lift gas 308 are introduced into the fast pyrolysis reactor 302 whereby the biomass 306 is converted to pyrolysis gas 310 comprising the lift gas 308 mixed with pyrolysis products. The pyrolysis gas 310 to the one or more liquid recovery components 304 and at least partially condensed to form a liquid product 312 and non-condensed pyrolysis gas 314. The one or more liquid recovery components 304 may comprise any of the one or more liquid recovery components disclosed herein and/or in the INCORPORATED REFERENCES. The biomass 306 can be one or more of the biomasses disclosed herein and/or in the INCORPORATED REFERENCES. The formaldehyde-free lift gas 308 can be a non-recirculated gas. The formaldehyde-free lift gas 308 can be an oxygen-free or low oxygen (for example less than 5 wt. % oxygen, less than 1 wt. % oxygen, or less than 0.5 wt. % oxygen) gas. The formaldehyde-free lift gas 308 can be a combustion flue gas (for example a combustion flue gas from an inorganic particle reheater). The pyrolysis gas 310 and/or the liquid product 312 can comprise one or more of the liquid product components disclosed herein and/or in the INCORPORATED REFERENCES. The non-condensed pyrolysis gas 314 can comprise formaldehyde. The non-condensed pyrolysis gas 314 can comprise a hydrocarbon. The non-condensed pyrolysis gas 314 can comprise carbon monoxide or carbon dioxide.

Figure 4:
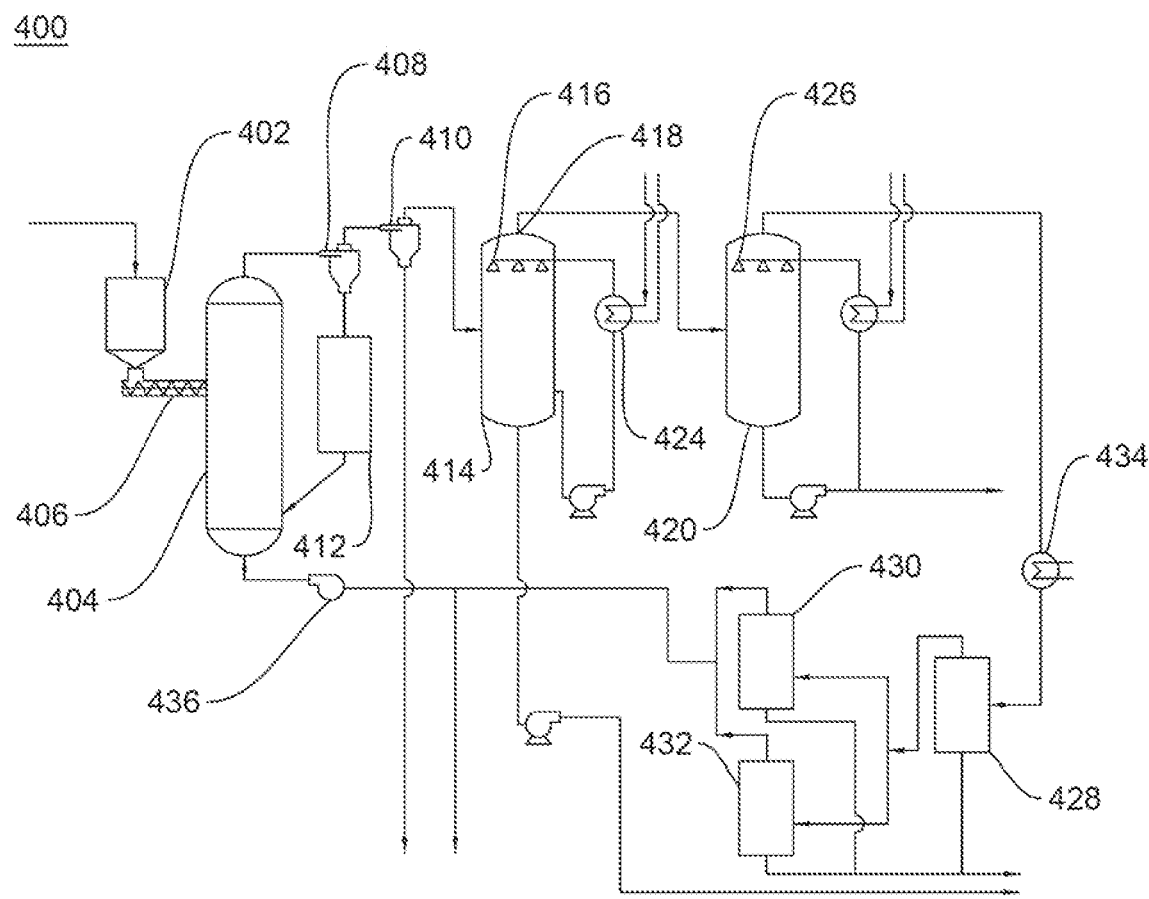
FIG. 4 is a schematic diagram of a rapid thermal processing system.

A rapid thermal processing system 400 for thermal conversion of biomass is shown in FIG. 4. A feed system 402 provides a regulated flow of solid biomass feedstock to an upflow fast pyrolysis reactor 404. Alternatively, the feed system 402 may be replaced with a liquid feed system comprising a liquid supply tank, pump, and spray equipment for the biomass to be introduced to the reactor 404 as a liquid stream (for example a biomass dissolved or suspended in water). The reactor can be operated at slightly above atmospheric pressure (i.e., sufficient pressure to overcome the back pressure of the downstream equipment), and the feed system 402 can provide material under slight pressure (1.2 atmospheres) while at the same time accepting feedstock material which is at atmospheric pressure.

When the feedstock is a particulate solid, a constant speed screw conveyor 406 constructed of stainless steel and provided with high temperature seals and bearings introduces the biomass to the reactor 404.

The reactor 404 mixes the biomass with an upward flowing stream of lift gas and hot heat carriers, e.g., sand, in a mixing zone of the reactor 404 to achieve thorough and rapid mixing and conductive heat transfer from the heat carriers to the biomass. The hot heat carriers instantly flash the feedstock into a hot vapor, which is cooled, condensed, and recovered downstream as a liquid product.

Rapid pyrolysis of the feedstock is initiated in the mixing zone under moderate temperatures (for example at a temperature in the range of 400° C. to 550° C.), through to a separation system comprising two cyclonic separators (408 and 410) located downstream of the reactor 404. The resident time in the reactor is preferably less than 5 seconds, and more preferably less than 2 seconds. The solid heat carriers along with by-product char are removed from the product vapor stream by the two cyclonic separators (408 and 410). The first cyclonic separator 408 separates the solid heat carriers and by-product char from the product stream. The solids that have been removed in the first separator 408 are directed to a reheater unit 412. In the reheater unit 412, the by-product char is converted by the addition of air to heat and combustion gases. Typically, there is more than sufficient heat generated by the combustion of by-product char and gas to satisfy the heat requirements of the thermal conversion process (external fuels, such as natural gas, are rarely used and typically for system start-up alone). The excess heat from the reheater can be productively used for other purposes, including biomass drying, steam generation, space heating, power generation, etc. The heat generated in the reheater elevates the temperature of the solid heat carriers, which can then be transferred to the feedstock material in the reactor 404 to achieve the necessary reaction temperatures.

The second separator 410 removes char that is not removed in the first separator 408 and passes a product vapor stream via an insulated duct to a quench condenser 414. Preferably, the product vapor stream is brought from a conversion temperature of approximately 350° C. to 600° C., to less than 100° C. in less than 1 s. More preferably, the hot vapor stream is reduced to less than 50° C. in less than 0.1 s (100 ms), and most preferably to a temperature of less than 50° C. in less than 20 ms. The quench condenser 414 is equipped with a liquid distributor 53 416 located in the upper portion of the condenser 414. Nonaqueous quench media that is at least partially immiscible with pyrolysis liquid condensate is circulated through the distributor 416 and allowed to "rain" down on the incoming vapor stream. Various types of distributor systems can be employed. Examples include, but are not limited to, vane, pipe, chimney, finger distributor, spray head, nozzle design, trays, packing, etc. Preferably, at least 10 gpm/sq. ft (gallons per minute/sq. ft) of column cross-sectional diameter of quench liquid is circulated through the collection column. More preferably, at least 50 to 100 gpm/sq. ft of column cross-sectional diameter of quench liquid is circulated through the collection column. The dense stream of liquid raining down the column not only serves to immediately cool and quench the incoming vapor but also provides nucleation sites for the collection of the liquid product. Typically, the hot vapor enters the quench condenser 414 just above the normal operating level of the collected liquid in the condenser 414. The vapor not collected in the condenser 414 along with the non-condensable gas exit the condenser 414 through a top exit port 418. This mode of operation is counter-current. In another mode of operation in which it is desired to minimize the length of the hot vapor piping the hot vapor enters through the upper portion of the condenser 414 and the vapor not collected in the condenser 414 along with the non-condensable gas exit through a port situated in the lower portion of the condenser 414 (just above the normal liquid level). This mode of operation is co-current. The condenser 414 may be equipped with a demister in the gas exit section of the column to reduce the carryover of liquid droplets into a secondary collection column 420.

Condensate of the pyrolysis gases flows to the lower portion of the condenser 414 with the nonaqueous quench, where the condensate and quench medium for two distinct phase. A portion of the condensate is drawn out from the condenser 414 as liquid product while a portion of the quench phase is pumped by a condenser pump 57 422 through a heat exchanger 424 to cool the quench, e.g., 30 to 50° C. The cooling medium for the heat exchanger 424 can be water. Other cooling means may be employed including a glycol system, an air cooler, or the like. The cooled quench is recirculated to the condenser 414.

The liquid product in the collection column is pumped out to product storage tanks (not shown) to maintain the desired liquid level. The collected liquid product provides a valuable liquid product, bio-oil, that can be used, e.g., for fuel and/or other commercial uses.

The vapor is rapidly quenched because the vapor and liquid product are thermally labile (chemically react at higher temperatures). By using a high liquid recirculation/quench rate, the incoming vapor is rapidly quenched, which avoids undesirable chemical reactions such as polymerization that occur at higher temperatures. Further, the high recirculation rate of the liquid product used for the quench media prevents the quench media from reaching undesirably high temperatures.

The secondary collection column 420 may use pyrolysis vapor condensate or a different quench medium via an overhead distribution system 426. Preferably, at least 10 gpm/sq. ft of column cross-sectional diameter of liquid is circulated through the secondary collection column 420. More preferably, at least 50 to 100 gpm/sq. ft of column cross-sectional diameter of quench liquid is circulated through the secondary collection column 420. The secondary collection column 420 may be equipped with a demister in the gas exit section of the secondary collection column 420 to reduce the carryover of liquid droplets, mist or aerosols into the downstream demister or filtering systems. The cross-sectional diameter of the secondary collection column 420 may be the same as the quench condenser secondary collection column 420. However, the secondary collection column 420 is typically smaller in diameter since greater superficial gas velocities will facilitate the removal of the fine droplets or aerosols in the demister section of the secondary collection column 420.

Mist, aerosols and non-condensable gas that exit the secondary collection column 420 are directed to a separate demister system 428. If the secondary collection column 420 is equipped with an internal demister unit, then the downstream separate demister system 428 may not be required. The demister system 428 preferably removes mist droplets that are greater than 3 microns. These droplets tend to be captured in the demister by inertial impaction. The particles, which are traveling in the gas stream, are unable to abruptly change direction along with the gas as the flow goes through the demisting system 428 due to their weight. As a result, they impact the fibers of the demister and are subsequently captured. Mist particles that come in contact with the demister fibers adhere by weak Van Der Waals forces. The accumulating impacting mist droplets tend to join together to form larger single droplets that finally fall to the lower portion of the demister vessel due to gravitational sedimentation.

The demister system 428 may comprise a series of mist eliminator units. The first unit is a vane mist eliminator which can remove about 99% of the mist as low as 10 microns. Next is a stainless steel wire mesh pad having a density of about 5 lbs/ft3 and a wire diameter of 0.011 inches (surface area of 45 ft2/ft3, and 99.0% voids). Other materials may be used besides steel including glass, alloy 20, Teflon, polypropylene, or the like. This is followed by a 9 lb/ft3 stainless steel wire mesh pad, again 0.011 inch diameter (surface area of 85 ft2/ft3, and 98.0% voids). The final mist eliminator unit is a co-knit style comprising a metal wire construction with fiberglass. The pad is 9 lb/ft3 with a wire diameter of 0.00036 inches (surface area of 3725 ft2/ft3, and 99.0% voids).

Fine aerosols (i.e., less than approximately 3 microns), condensed particles of greater than 3 microns that evaded the demister system 428, and non-condensable gas from either the secondary condensing column 60 or the demister system 428 pass to a final filtering system. The filter system may comprise two fiber beds 430 and 432 set up in parallel, as shown. Again, as was the case with the demister system 428, particles larger than about 3 microns are captured by inertial impaction. Condensed particles between 1 and 3 microns tend to be captured through interception in which the particles follow the non-condensable gas stream line that comes within about one particle radius of the surface of a fiber. Particles of less than 1 micron are captured through diffusion or Brownian movement in which the particles have a tendency to attach themselves to the fibers of the filters (430 and 432) due to their random motion. Again, captured particles tend to join together to form larger liquid droplets. However, the pressure drop across the filters (430 and 432) may exceed predetermined limits before a sufficient quantity of material has drained to the lower section of the filter vessel. In addition, re-entrainment of collected material can occur as the localized loading of liquid increases the effective open cross-sectional area of the filter decreases thereby increasing the flow of gas through the remaining open areas. This increase flow of gas leads to increased velocities that can lead to higher than desired pressure drops and possibly re-entrainment, and loss of captured liquid. Therefore, the filters (430 and 432) can consist of more than one filter unit which can be set up in parallel or in series as required. Typically two filters are employed in parallel in which one filter unit is on-line at any one time. A filter unit may remain on-line for a period of about 8 to 24 hours (typically 12 hours). When a filter is switched off-line it is allowed to drain. The pressure drop across the filter unit can also dictate the period of time that the unit is allowed to remain on-line. Pressure drops that exceed predetermined limits (typically 100 inches of water column) can lead to failure of filter elements (i.e., tear holes can develop in the fabric).

Since the collected mists and aerosol liquid can tend to be relatively viscous at ambient conditions a reheat exchanger 434 can be employed between the secondary condenser column 420 and the demister system 428 and fiber bed filters (430 and 432). Alternatively, if the demister is incorporated in the secondary condenser column 420, the reheat exchanger will be installed upstream of the fiber bed filters (430 and 432) only. The reheat exchanger 434 is used to slightly elevate the temperature of the vapor stream (up to about 60-65° C.) and enable a sufficient viscosity reduction of the captured liquids in the downstream systems to allow adequate drainage.

The gas filtered through the filters (430 and 432) is recycled back to the reactor 404 by a reactor blower 436. To provide lift gas. Alternatively, a non-recycled, formaldehyde-free lift gas (for example 100% nitrogen gas from a cryogenic source) may be provided.

INCORPORATION BY REFERENCE

Without limitation, the following documents are hereby incorporated, in their entirety, by reference: U.S. Pat. Nos. 2,307,937; 4,101,412; 4,876,108; 5,135,770; 5,252,188; 5,292,541; 5,397,582; 5,840,362; 5,961,786; 6,485,841; 7,572,362; U.S. Patent Application Publication Nos. 2004/0022912; 2012/0022171; 2014/0053456; 2015/0191656; 2016/0002137; 2016/0024037; 2017/0275545; 2018/0334618; International (PCT) Patent Application Publication Nos. WO 1998/000935; WO 2018/017664; and European Patent No. EP1311615 (collectively, the "INCORPORATED REFERENCES").

EXAMPLES

In Examples 1-2 and Comparative Example A, glucose fast pyrolysis experiments were performed in a bench scale reactor and liquid products obtained from a sequence of recovery units that included a quench condenser, a secondary condenser (chiller), a fiber bed filter, and a demister. In Comparative Samples 1-2, liquid samples obtained from operating pyrolysis plant were obtained and analyzed. Results are shown in Table 1. Analysis details are shown in Tables 2-3.

TABLE 1

Results for liquid samples obtained from quench condenser.

| Ratio | Example 1[1] | Example 2[2] | Comparative Example A[3] | Aqueous Browning Agent Samples from Operating Pyrolysis Plant[4] | |
|---|---|---|---|---|---|
| | | | | Sample 1 | Sample 2 |
| Hydroxyacetaldehyde:BRIX (wt. %/° BX) | 0.47 | 0.50 | 0.50 | 0.68 | 0.60 |
| Formaldehyde:Hydroxyacetaldehyde (w/w) | 0.018 | 0.006 | 0.076 | 0.03 | 0.03 |
| Formaldehyde:BRIX (ppm/° BX) | 84 | 31 | 382 | 172 | 178 |

[1] 65° BX solution of glucose was pyrolyzed in a continuous upflow reactor utilizing sand heat transfer particles and once-through nitrogen lift gas, and pyrolysis vapors quenched with liquid dodecane in a quench condenser.
[2] Solid glucose particles were pyrolyzed in a continuous upflow reactor utilizing sand heat transfer particles and once-through nitrogen lift gas, and pyrolysis vapors quenched with liquid dodecane in a quench condenser.
[3] 65° BX solution of glucose was pyrolyzed in a continuous upflow reactor utilizing sand heat transfer particles and once-through nitrogen lift gas, and pyrolysis vapors quenched with liquid water in a quench condenser.
[4] A solution of simple sugars was pyrolyzed in continuous upflow reactor utilizing sand heat transfer particles and recirculated lift gas, and pyrolysis vapors quenched with liquid water in a quench condenser.

TABLE 2

Analysis of fast pyrolysis products in Examples 1-2 and Comparative Example A[1]

| Product Characteristics | Liquid Product Fractions | | | | Product Characteristics, cont'd | Liquid Product Fractions | | | |
|---|---|---|---|---|---|---|---|---|---|
| | Condenser | Chiller | Filter/Demister[2] | Quench Liquid | | Condenser | Chiller | Filter/Demister | Quench Liquid |
| EXAMPLE 1 | | | | | | | | | |
| | Feed Rate, lb/hr | | | 5.1 | Reactor Temperature, ° C. | 458 | | | |
| | Inlet Feed Temperature, ° C. | | | 80 | Condenser Temperature, ° C. | 50 | | | |
| Formaldehyde, ppm | 4850 | NT | NT | <340 | Water, wt. % | 35.4 | 92.3 | 36.5 | N/A |
| Hydroxyacetaldehyde, wt. % | 27.0 | 0.68 | 13.8 | NT | Ash, wt. % | 0.17 | <0.01 | 0.10 | N/A |
| BRIX, ° BX | 57.6 | 5.8 | 57.3 | NT | Solids, wt. % | 0.22 | 0.01 | 0.09 | N/A |
| Acetic acid equiv., wt. %[3] | 1.9 | 0.6 | 1.8 | NT | Specific Gravity | 1.25 | 1.10 | 2.25 | NT |
| Carbonyl content, g/100 mL[4] | 44.7 | 7.5 | 50.7 | NT | pH | 2.9 | 2.7 | 2.8 | N/A |
| EXAMPLE 2 | | | | | | | | | |
| | Feed Rate, lb/hr | | | 3.9 | Reactor Temperature, ° C. | 475 | | | |
| | Inlet Feed Temperature, ° C. | | | — | Condenser Temperature, ° C. | 55 | | | |
| Formaldehyde, ppm[3] | 2530 | NT | NT | NT | Water, wt. % | 9.1 | 77.4 | 11.6 | N/A |
| Hydroxyacetaldehyde, wt. % | 40.7 | 4.61 | 34.2 | NT | Ash, wt. % | 2.75 | 0.02 | NT | N/A |

TABLE 2-continued

Analysis of fast pyrolysis products in Examples 1-2 and Comparative Example A[1]

| Product Characteristics | Liquid Product Fractions | | | | Product Characteristics, cont'd | Liquid Product Fractions | | | |
|---|---|---|---|---|---|---|---|---|---|
| | Condenser | Chiller | Filter/Demister[2] | Quench Liquid | | Condenser | Chiller | Filter/Demister | Quench Liquid |
| BRIX, °BX | 82.1 | 18.3 | 77.1 | NT | Solids, wt. % | 2.62 | 0.01 | NT | N/A |
| Acetic acid equiv., wt. % | 2.4 | 2.0 | 2.2 | NT | Specific Gravity | 1.4 | 1.1 | 1.3 | NT |
| Carbonyl content, g/100 mL | 106.5 | 39.5 | 97.8 | NT | pH | 3.2 | 2.4 | 3.4 | N/A |

COMPARATIVE EXAMPLE A

| | Feed Rate, lb/hr | | 4.9 | | Reactor Temperature, °C. | 485 | | | |
|---|---|---|---|---|---|---|---|---|---|
| | Inlet Feed Temperature, °C. | | 80 | | Condenser Temperature, °C. | 37 | | | |
| Formaldehyde, ppm[3] | 6030 | NT | NT | N/A | Water, wt. % | 85.5 | 99.1 | 44.4 | N/A |
| Hydroxyacetaldehyde, wt. % | 7.91 | ND | 6.91 | N/A | Ash, wt. % | 0.04 | <0.01 | 0.18 | N/A |
| BRIX, °BX | 15.8 | 2.1 | 53.7 | N/A | Solids, wt. % | 0.82 | 0.02 | 0.10 | N/A |
| Acetic acid equiv., wt. % | 0.6 | 0.3 | 1.9 | N/A | Specific Gravity | 1.06 | 1.02 | 1.21 | N/A |
| Carbonyl content, g/100 mL | 13.6 | 2.3 | 78 | N/A | pH | 3.0 | 3.1 | 3.2 | N/A |

[1]Liquid samples collected from a quench condenser, chiller, fiber bed filter, and demister.
[2]Liquid samples from fiber bed filter and demister were combined for analysis.
[3]Acetic Acid Equivalents, inclusive of acetic acid, formic acid, and propionic acid.
[4]Liquid product components containing carbonyl functional group.

TABLE 3

Analysis of aqueous browning agent samples obtained from operating pyrolysis plant[1]

| Product Characteristics | Liquid Product Fractions | | | | Product Characteristics, cont'd | Liquid Product Fractions | | | |
|---|---|---|---|---|---|---|---|---|---|
| | Primary Quench Condenser | Secondary Quench Condenser | Filter Bed | Demister | | Primary Quench Condenser | Secondary Quency Condenser | Filter Bed | Demister |
| | | | | SAMPLE 1 | | | | | |
| Formaldehyde, ppm | 8500 | NT | NT | NT | Water, wt. % | N/A | N/A | N/A | N/A |
| Hydroxyacetaldehyde, wt. % | 33.6 | 12.9 | 7.4 | 10.3 | Ash, wt. % | N/A | N/A | N/A | N/A |
| BRIX, °BX | 49.3 | 53.5 | 53.0 | 61 | Solids, wt. % | N/A | N/A | N/A | N/A |
| Acetic acid equiv., wt. % | 2.4 | 2.7 | 3.6 | 3.8 | Specific Gravity | 1.22 | 1.23 | 1.22 | 1.27 |
| Carbonyl content, g/100 mL | 71.4 | 93.7 | 77.0 | 91.9 | pH | N/A | N/A | N/A | N/A |
| | | | | SAMPLE 2 | | | | | |
| Formaldehyde, ppm | 8800 | NT | NT | NT | Water, wt. % | N/A | N/A | N/A | N/A |
| Hydroxyacetaldehyde, wt. % | 29.5 | 13.0 | 7.3 | 10.5 | Ash, wt. % | N/A | N/A | N/A | N/A |
| BRIX, °BX | 49.3 | 53.3 | 53.0 | 61 | Solids, wt. % | N/A | N/A | N/A | N/A |
| Acetic acid equiv., wt. %[3] | 2.4 | 2.8 | 3.7 | 3.9 | Specific Gravity | 1.22 | 1.23 | 1.23 | 1.27 |
| Carbonyl content, g/100 mL[4] | 73.3 | 89.3 | 80.8 | 88.6 | pH | N/A | N/A | N/A | N/A |

[1]Samples obtained from quench condenser.
2. Liquid product fractions of fiber bed filter and demister were combined for analysis.
[3]Acetic Acid Equivalents, inclusive of acetic acid, formic acid, and propionic acid.
[4]Liquid product components containing carbonyl functional group.

All publications and patent applications mentioned in this specification are herein incorporated by reference to the same extent as if each individual publication or patent application was specifically and individually indicated to be incorporated by reference.

While preferred embodiments of the present invention have been shown and described herein, it will be obvious to those skilled in the art that such embodiments are provided by way of example only. It is intended that the following claims define the scope of the invention and that methods and structures within the scope of these claims and their equivalents be covered thereby.

What is claimed is:

1. A method for producing a low-formaldehyde product having (a) a ratio of no more than 150 ppm formaldehyde per 1° BX of the low-formaldehyde product, and (b) a ratio of between 0.1 wt. % hydroxyacetaldehyde per 1° BX of the low-formaldehyde product and 0.5 wt. % hydroxyacetaldehyde per 1° BX of the low-formaldehyde product, the method comprising:
   i) pyrolyzing a biomass solution to form gaseous pyrolysis products;
   ii) condensing a portion of the gaseous pyrolysis products to form the low-formaldehyde product, comprising: contacting the gaseous pyrolysis products with a non-aqueous coolant; and iii) separating at least a portion of the low-formaldehyde product from the nonaqueous coolant,
wherein the low-formaldehyde product contains hydroxyacetaldehyde and has a ratio of formaldehyde-to-hydroxyacetaldehyde of no more than 0.1 (w/w),
wherein a temperature of the condensing is less than 80° C.,
wherein the nonaqueous coolant is selected from the group consisting of an unsaturated liquid hydrocarbon, a saturated liquid hydrocarbon, hexane, heptane, dodecane, a vegetable oil, a silicone oil, and a combination thereof, and
wherein the biomass solution comprises one or more sugars and/or one or more starches at a BRIX value of 40° BX to 90° BX.

2. The method of claim 1, wherein the biomass solution comprises a simple sugar.

3. The method of claim 1, wherein the biomass solution comprises an impure mixture of different sugars.

4. The method of claim 1, wherein the biomass solution comprises one or more starches selected from the group consisting of corn starch, potato starch, wheat starch, oat starch, tapioca starch and rice starch.

5. The method of claim 1, wherein the biomass solution further comprises a cellulosic biomass.

6. The method of claim 1, wherein the biomass solution comprises a particulate solid and is provided in a carrier gas.

7. The method of claim 1, wherein the low-formaldehyde product is a browning agent.

8. The method of claim 1, wherein the low-formaldehyde product is a microwave browning agent.

9. The method of claim 1, wherein the low-formaldehyde product is a binder.

10. The method of claim 1, wherein the low-formaldehyde product may be processed into a binder.

11. The method of claim 1, wherein a binder is derived from the low-formaldehyde product.

12. The method of claim 1, wherein the low-formaldehyde product is a chemical.

13. The method of claim 1, wherein the low-formaldehyde product may be processed into a chemical.

14. The method of claim 1, wherein a chemical is derived from the low-formaldehyde product.

15. The method of claim 1, wherein the low-formaldehyde product is rich in hydroxyacetaldehyde.

16. The method of claim 1, wherein the low-formaldehyde product is a solvent.

17. The method of claim 1, wherein the low-formaldehyde product may be processed into a plastic.

18. A method for producing a low-formaldehyde liquid product having (a) a ratio of no more than 150 ppm formaldehyde per 1° BX of the low-formaldehyde liquid product, and (b) a ratio of between 0.1 wt. % hydroxyacetaldehyde per 1° BX of the low-formaldehyde product and 0.5 wt. % hydroxyacetaldehyde per 1° BX of the low-formaldehyde product, the method comprising:
i) pyrolyzing a biomass solution to form gaseous pyrolysis products;
ii) introducing the gaseous pyrolysis products into a separation unit;
iii) recirculating a liquid coolant having a water solubility at 25° C. of less than 100 ppm water from an outlet of the separation unit to an inlet of the separation unit; and
iv) recovering a low-formaldehyde liquid product comprising at least 50 wt. % of the gaseous pyrolysis products from the separation unit,
wherein the low-formaldehyde product contains hydroxyacetaldehyde and has a ratio of formaldehyde-to-hydroxyacetaldehyde of no more than 0.1 (w/w),
a temperature of separating in the separation unit is less than 80° C.,
the liquid coolant is selected from the group consisting of an unsaturated liquid hydrocarbon, a saturated liquid hydrocarbon, hexane, heptane, dodecane, a vegetable oil, a silicone oil, and a combination thereof, and
the biomass solution comprises one or more sugars and/or one or more starches at a BRIX value of 40° BX to 90° BX.

19. A method for producing a low-formaldehyde liquid product having (a) a ratio of no more than 150 ppm formaldehyde per 1° BX of the low-formaldehyde liquid product, and (b) a ratio of between 0.1 wt. % hydroxyacetaldehyde per 1° BX of the low-formaldehyde product and 0.5 wt. % hydroxyacetaldehyde per 1° BX of the low-formaldehyde product, the method comprising:
i) pyrolyzing a biomass solution to form a gaseous pyrolytic stream comprising water;
ii) introducing the gaseous pyrolytic stream into a separation unit;
iii) recirculating a substantially water-free liquid coolant stream from an outlet of the separation unit to an inlet of the separation unit; and
iv) recovering substantially all of the water present in the gaseous pyrolytic stream from the separation unit in a first stream consisting of the liquid product and a second stream consisting of a non-condensed portion of the gaseous pyrolytic stream,
wherein the low-formaldehyde product contains hydroxyacetaldehyde and has a ratio of formaldehyde-to-hydroxyacetaldehyde of no more than 0.1 (w/w),
a temperature of separating in the separation unit is less than 80° C.,
the substantially water-free liquid coolant stream comprises at least one selected from the group consisting of an unsaturated liquid hydrocarbon, a saturated liquid hydrocarbon, hexane, heptane, dodecane, a vegetable oil, and a silicone oil, and
the biomass solution comprises one or more sugars and/or one or more starches at a BRIX value of 40° BX to 90° BX.

* * * * *